United States Patent
Cates et al.

(10) Patent No.: US 7,236,821 B2
(45) Date of Patent: Jun. 26, 2007

(54) CHRONICALLY-IMPLANTED DEVICE FOR SENSING AND THERAPY

(75) Inventors: Adam W. Cates, Minneapolis, MN (US); Paul V. Goode, San Diego, CA (US); Scott T. Mazar, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 21 days.

(21) Appl. No.: 10/079,056

(22) Filed: Feb. 19, 2002

(65) Prior Publication Data

US 2003/0158584 A1 Aug. 21, 2003

(51) Int. Cl.
*A61N 1/00* (2006.01)
(52) U.S. Cl. .......................................................... 607/2
(58) Field of Classification Search ............. 607/1–156
See application file for complete search history.

(56) References Cited

U.S. PATENT DOCUMENTS

| | | | |
|---|---|---|---|
| 3,692,027 A | 9/1972 | Ellinwood, Jr. ............. 128/260 |
| 4,003,379 A | 1/1977 | Ellinwood, Jr. ............. 128/260 |
| 4,146,029 A | 3/1979 | Ellinwood, Jr. ............. 128/260 |
| 4,281,664 A | 8/1981 | Duggan ....................... 128/696 |
| 4,299,220 A | 11/1981 | Dorman ...................... 128/260 |
| 4,544,371 A | 10/1985 | Dormandy, Jr. et al. .... 604/891 |
| 4,556,063 A | 12/1985 | Thompson et al. .... 128/419 PT |
| 4,686,987 A | 8/1987 | Salo et al. ............ 128/419 PG |
| 4,800,882 A | 1/1989 | Gianturco |
| 4,871,351 A | 10/1989 | Feingold ....................... 604/66 |
| 4,907,336 A | 3/1990 | Gianturco |
| 4,936,281 A | 6/1990 | Stasz |
| 4,987,897 A | 1/1991 | Funke .................. 128/419 PG |
| 4,994,033 A | 2/1991 | Shockey et al. |
| 5,040,533 A | 8/1991 | Fearnot ................. 128/419 PG |
| 5,041,107 A | 8/1991 | Heil, Jr. .................... 604/891.1 |
| 5,042,497 A | 8/1991 | Shapland ..................... 600/509 |
| 5,078,736 A | 1/1992 | Behl |
| 5,087,243 A | 2/1992 | Avitall ......................... 604/20 |
| 5,178,618 A | 1/1993 | Kandarpa |

(Continued)

FOREIGN PATENT DOCUMENTS

| | | |
|---|---|---|
| EP | 0467695 A2 | 1/1992 |
| EP | 1050265 | 11/2000 |
| WO | WO-97/33513 | 9/1997 |
| WO | WO-0007497 A1 | 2/2000 |
| WO | WO-01/30436 | 5/2001 |

OTHER PUBLICATIONS

Burns, Brent E., "Fabrication Technology for a Chronic In-Vivo Pressure Sensor", *1984 International Electron Devices Meeting Technical Digest*, (1984),210-212.

(Continued)

*Primary Examiner*—Scott M. Getzow
(74) *Attorney, Agent, or Firm*—Finnegan, Henderson, Farabow, Garrett & Dunner, L.L.P.

(57) ABSTRACT

Systems, devices and methods are provided for providing sensing and therapy functions using a chronically-implanted device. According to one embodiment, the device includes a structure adapted to be chronically placed within a biosystem, and further includes sensing circuitry and therapy-providing circuitry attached to the structure. The sensing circuitry is adapted to sense mechanical parameters in the biosystem. The therapy-providing circuitry is adapted to provide therapy to the biosystem. According to various embodiments of the device, the sensing circuitry is further adapted to sense electrical and/or chemical parameters in the biosystem, and/or is adapted to provide electrical therapy and/or to provide drug-eluting therapy. One embodiment of the device includes a stent-like structure adapted to be chronically placed intravascularly in the biosystem.

172 Claims, 12 Drawing Sheets

U.S. PATENT DOCUMENTS

| | | | |
|---|---|---|---|
| 5,220,917 A | 6/1993 | Cammilli et al. | 128/419 D |
| 5,269,301 A | 12/1993 | Cohen | 607/6 |
| 5,284,136 A | 2/1994 | Hauck et al. | 607/24 |
| 5,292,321 A | 3/1994 | Lee | |
| 5,353,800 A | 10/1994 | Pohndorf et al. | 128/673 |
| 5,368,028 A | 11/1994 | Palti | 128/635 |
| 5,417,717 A | 5/1995 | Salo et al. | |
| 5,460,605 A | 10/1995 | Tuttle et al. | 604/67 |
| 5,496,360 A | 3/1996 | Hoffmann et al. | 607/120 |
| 5,499,971 A | 3/1996 | Shapland et al. | 604/53 |
| 5,556,421 A | 9/1996 | Prutchi et al. | 607/36 |
| 5,607,418 A | 3/1997 | Arzbaecher | 604/891.1 |
| 5,607,463 A | 3/1997 | Schwartz et al. | 623/1.44 |
| 5,634,899 A | 6/1997 | Shapland et al. | 604/51 |
| 5,637,113 A | 6/1997 | Tartaglia et al. | |
| 5,662,689 A | 9/1997 | Elsberry et al. | 607/5 |
| 5,690,682 A | 11/1997 | Buscemi et al. | 607/3 |
| 5,693,085 A | 12/1997 | Buirge et al. | |
| 5,730,125 A | 3/1998 | Prutchi et al. | 128/637 |
| 5,766,192 A | 6/1998 | Zacca | |
| 5,775,338 A | 7/1998 | Hastings | |
| 5,800,498 A | 9/1998 | Obino et al. | 607/123 |
| 5,814,089 A | 9/1998 | Stokes et al. | 607/32 |
| 5,817,131 A | 10/1998 | Elsberry et al. | 607/5 |
| 5,833,603 A | 11/1998 | Kovacs et al. | 600/317 |
| 5,836,935 A | 11/1998 | Ashton et al. | 604/891.1 |
| 5,846,218 A | 12/1998 | Brisken et al. | |
| 5,876,433 A | 3/1999 | Lunn | |
| 5,893,881 A | 4/1999 | Elsberry et al. | 607/5 |
| 5,899,917 A | 5/1999 | Edwards et al. | |
| 5,906,636 A | 5/1999 | Casscells, III et al. | |
| 5,921,954 A | 7/1999 | Mohr, Jr. et al. | |
| 5,925,066 A | 7/1999 | Kroll et al. | 607/3 |
| 5,944,710 A | 8/1999 | Dev et al. | |
| 5,954,761 A | 9/1999 | Macheck et al. | 607/126 |
| 5,967,986 A | 10/1999 | Cimochowski et al. | 600/454 |
| 5,972,029 A | 10/1999 | Fuisz | |
| 5,980,566 A | 11/1999 | Alt et al. | |
| 5,991,668 A | 11/1999 | Leinders et al. | 607/125 |
| 6,053,913 A | 4/2000 | Tu et al. | |
| 6,102,908 A | 8/2000 | Tu et al. | |
| 6,141,588 A | 10/2000 | Cox et al. | 607/9 |
| 6,168,801 B1 | 1/2001 | Heil, Jr. et al. | 424/426 |
| 6,179,824 B1 | 1/2001 | Eggers et al. | |
| 6,206,914 B1 | 3/2001 | Soykan et al. | 623/1.42 |
| 6,231,516 B1 | 5/2001 | Keilman et al. | 600/485 |
| 6,236,889 B1 * | 5/2001 | Soykan et al. | 607/30 |
| 6,237,398 B1 | 5/2001 | Porat et al. | 73/54.09 |
| 6,254,573 B1 | 7/2001 | Haim et al. | 604/157 |
| 6,272,377 B1 | 8/2001 | Sweeney et al. | |
| 6,277,078 B1 | 8/2001 | Porat et al. | 600/486 |
| 6,278,894 B1 | 8/2001 | Salo et al. | |
| 6,298,272 B1 | 10/2001 | Peterfeso et al. | 607/120 |
| 6,309,370 B1 | 10/2001 | Haim et al. | 604/66 |
| 6,317,615 B1 | 11/2001 | KenKnight et al. | 600/372 |
| 6,361,522 B1 | 3/2002 | Scheiner et al. | 604/67 |
| 6,361,780 B1 | 3/2002 | Ley et al. | 424/400 |
| 6,442,413 B1 | 8/2002 | Silver | 600/345 |
| 6,443,949 B2 | 9/2002 | Altman | 606/41 |
| 6,453,195 B1 | 9/2002 | Thompson | 607/3 |
| 6,459,917 B1 | 10/2002 | Gowda et al. | 600/345 |
| 6,468,263 B1 | 10/2002 | Fischell et al. | |
| 6,511,477 B2 | 1/2003 | Altman et al. | 606/41 |
| 6,519,488 B2 | 2/2003 | KenKnight et al. | 600/372 |
| 6,622,044 B2 * | 9/2003 | Bange et al. | 607/27 |
| 6,645,145 B1 * | 11/2003 | Dreschel et al. | 600/443 |
| 6,648,881 B2 | 11/2003 | KenKnight et al. | |
| 6,689,117 B2 | 2/2004 | Sweeney et al. | 604/503 |
| 6,748,274 B2 * | 6/2004 | Levine et al. | 607/32 |
| 6,829,504 B1 * | 12/2004 | Chen et al. | 607/4 |
| 6,845,267 B2 * | 1/2005 | Harrison et al. | 607/3 |
| 2001/0000802 A1 | 5/2001 | Soykan et al. | 623/1.13 |
| 2002/0026228 A1 | 2/2002 | Schauerte | 607/122 |
| 2002/0099328 A1 | 7/2002 | Scheiner et al. | |
| 2003/0004403 A1 | 1/2003 | Drinan et al. | 600/301 |
| 2003/0009204 A1 * | 1/2003 | Amundson et al. | 607/60 |
| 2003/0060854 A1 | 3/2003 | Zhu | 607/25 |
| 2003/0069606 A1 | 4/2003 | Girouard | 607/3 |
| 2003/0153952 A1 | 8/2003 | Auricchio et al. | |
| 2004/0002739 A1 | 1/2004 | Cates et al. | 607/6 |
| 2004/0093034 A1 | 5/2004 | Girouard et al. | |

OTHER PUBLICATIONS

Carr, William N., et al., "Integrated Pressure Sensor With Remote Power Source and Remote Readout", *The 8th International Conference on Solid-State Sensors and Actuators and Eurosensors IX, Digest of Technical Papers*, Stockholm, Sweden, (Jun. 25-29, 1995),624-627.

Chau, Hin-Leung, et al., "An Ultraminiature Solid-State Pressure Sensor for a Cardiovascular Catheter", *IEEE Transactions on Electron Devices*, (Dec. 1988),2355-2362.

Pastore, Joseph M., "Method And Apparatus For Modulating Cellular Metabolism During Post-Ischemia Or Heart Failure", U.S. Appl. No. 10/645,823, filed Aug. 21, 2003, 46 pages.

Spiegel, Egbert, "A CMOS Sensor and Signal Conversion Chip for Monitoring Arterial Blood Pressure and Temperature", *IEEE International Solid-State Circuits Conference.*, (Feb. 20, 1992),126-127.

Ziaie, Babak, et al., "A Single-Channel Implantable Microstimulator for Functional Neuromuscular Stimulation", *IEEE Transactions on Biomedical Engineering*, 44, (Oct. 1997),909-920.

\* cited by examiner

CHRONICALLY-IMPLANTED DEVICE FOR SENSING AND THERAPY

TECHNICAL FIELD OF THE INVENTION

This invention relates generally to the field of medical devices and, more particularly, to intravascular devices.

BACKGROUND OF THE INVENTION

A correlation exists between cardiac electrical abnormalities and coronary vascular abnormalities. These abnormalities often coexist with each other. For example, patients who receive an implantable cardioverter defibrillator (ICD) often also have coronary artery disease (CAD). Ischemia is associated with CAD. One definition of ischemia is a reduced blood flow or a localized tissue anemia due to obstruction of the inflow of arterial blood. Ischemia is capable of initiating electrical arrhythmias; and electrical abnormalities are capable of altering hemodynamics and compromising blood flow. Present therapies typically address one abnormality or the other despite this correlation between cardiac electrical abnormalities and coronary vascular abnormalities.

Cardiac electrical abnormalities are addressed by cardiac stimulus devices such as pacemakers and ICDs. These cardiac stimulus devices monitor electrical activity and restore normal function by delivering pacing strength or defibrillation shock strength electrical pulses. These devices provide a sensing function by sensing the electrical function of the heart. That is, these devices are capable of sensing arrhythmias and intervening electrically. Most cardiac stimulus devices use intracavitary leads placed transvenously for sensing, pacing, and shocking. Now, leads are also being placed intravenously. However, conventional cardiac stimulus devices do not monitor the mechanical performance of the heart or otherwise provide a mechanical performance.

Conventional pacemakers often include an electronics assembly housed in a hermetically sealed enclosure, and one or more leads which connect the pacer directly to the heart tissues to be stimulated and sensed. The electronics assembly is able to be implanted in a suitable area of the body, commonly the upper thorax, because of the length of the lead used, which may be 18 to 30 inches long, for example.

One end of the lead connects to the pacer, while the other end of the lead, referred to as the "distal" end, is attached to an interior surface of one of the chambers of the heart, for example. One or more electrodes typically are disposed at the distal end of the lead through which electrical pulses are delivered to the heart at the site of the electrodes and/or from which sensing occurs. During implantation of conventional pacer systems, it is a common procedure for the physician to insert a stiff wire ("stylette") through the center of the lead and then to "snake" the lead though a predetermined path to the heart. Often the leads are implanted by guiding them through blood vessels into one or more chambers of the heart. The leads typically pass through valves that separate the atrial from the ventricular chambers.

Although leads have been used for many years in conjunction with implanted pacemakers and defibrillators both to stimulate the heart to beat as well as to sense the electrical activity of the heart, the use of leads is not problem free. For instance, the implantation avenues available for leads to be routed to and through the heart may be limited by the lumenal diameter of the vessels leading to the heart or by valves in the heart, and the ability to chronically fix the lead tends to be influenced by the anchorage available (e.g. trabeculas). Further, because the pressures in the right cardiac chambers are markedly lower than the pressures in the left cardiac chambers, it has been preferred to introduce leads into the right side of the heart because of the reduced risk of blood loss. Thus, for these practical reasons, a physician typically only implants the leads in a relatively few preselected sites in the heart. These sites, however, are not necessarily the optimal sites, but are chosen as a compromise between the complications described above and the patient's cardiac problem. Rather than monitoring the electrical activity in the right ventricle, monitoring the left ventricle's electrical activity, for example, might be preferred instead.

Additionally, it is desired for some applications to sense electrical activity at three, four, or more sites in the heart. Some pacers are implanted with four leads permitting sensing at four different sites in the heart. Four leads tend to be difficult to implant as they occupy a relatively large volume in the blood vessels through which they are passed and sometimes have to be steered along circuitous routes. Further, it is becoming increasingly desirable to sense at more locations in or on the heart than is possible with conventional pacer-lead combinations. It would thus be highly beneficial to have a stimulation and sensing system that provides the diagnostic and therapeutic functions provided by conventional cardiac stimulators yet which employs fewer interconnecting leads, than required by conventional devices, or which can function without using any leads.

U.S. Pat. No. 6,141,588, which issued to Cox et al. and is assigned to Intermedics, Inc., relates to a satellite pacing electrode system and is hereby incorporated by reference in its entirety. This satellite pacing electrode system is a system of remote electrodes that communicate with and are controlled by a central unit. The disclosed satellite pacing system uses epicardial electrodes that are in direct contact with myocardium. Epicardial placement of these electrodes at multiple sites often involves open-chest surgery. It would thus be highly beneficial to have a stimulation and sensing system that provides the diagnostic and therapeutic functions provided by epicardial electrodes of Cox et al., yet which involves less invasive surgery.

Coronary vascular abnormalities are addressed by blood flow and blood pressure monitors and stents, for example. However, these device are unable to sense arrhythmias and electrically intervene. Catheter-based blood flow and pressure monitors presently exist for acute measurements. These monitors provide a sensing function by sensing the mechanical performance of the heart. Examples of these catheter-based monitors include Millar catheters, and Swann-Ganz catheters. However, these catheter-based devices cannot be used chronically; that is, they cannot be implanted and used for long durations. Metal stents are placed intravascularly to reopen arteries in balloon angioplasty operations. However, the function of conventional stents is to prevent restenosis, i.e. to prevent the arteries from narrowing or constricting again.

Given the correlation between cardiac electrical abnormalities and coronary vascular abnormalities, it is desired to provide a chronically-implanted cardiac stimulus device with sensing capabilities to determine cardiac electrical abnormalities and coronary vascular abnormalities for improving arrhythmia therapy. More generally, it is desired to provide a chronically-implanted device that is capable of performing one or various combinations of mechanical, electrical, and chemical sensing and to provide a chronically-implanted device that is also capable of providing appropriate therapy, such as electrical or drug therapy, based on an event sensed by the chronically implanted device or by other devices within a system of devices. Additionally, there is a need to provide a chronically-implanted stimulus device that is capable of being implanted in a large number of desirable locations using less invasive procedures.

SUMMARY OF THE INVENTION

The above mentioned problems are addressed by the present subject matter and will be understood by reading and studying the following specification. The present subject matter provides a chronically-implanted device that is capable of providing sensing and therapy functions, including mechanical, electrical and chemical sensing functions, and mechanical, electrical and drug-eluting therapy functions, and various combinations thereof. According to one embodiment, the electrical stimulation functions provided by the intravascular device involves only a minimally invasive surgery, even when several electrodes are placed for multisite pacing. Strategies that incorporate multisite pacing are believed to offer therapeutic advantages, including improved hemodynamics and possible arrhythmia prevention by improved antitachycardia pacing schemes. According to one embodiment, the chronically-implanted device is an intravascular device that has a structure of a stent for preventing restenosis. However, the invention is not so limited.

According to one embodiment, the sensor functions provided by the device are capable of providing continuous intravascular measurements, such as blood pressure, blood flow and vessel size. According to one embodiment, the chronically-implanted device, or system of devices, communicates with a central unit, such as an implantable device, and monitors blood flow, blood pressure, and vessel inner diameter. According to various embodiments, one or more functions are capable of being performed including, but not limited to, detecting acute ischemia onset, providing an indication of restenosis, providing an evaluation of cardiac function, discriminating between a ventricular tachycardia (VT) that is hemodynamically stable versus a VT that compromises blood flow, and providing a determination of electromechanical dissociation.

One aspect of the present invention is a device. According to one embodiment, the device includes a structure adapted to be chronically placed within a biosystem, and further includes sensing circuitry and therapy-providing circuitry attached to the structure. The sensing circuitry is adapted to sense mechanical parameters in the biosystem. The therapy-providing circuitry is adapted to provide therapy to the biosystem.

According to various embodiments of the device, the sensing circuitry is further adapted to sense electrical and/or chemical parameters in the biosystem. According to various embodiments of the device, the therapy-providing circuitry is adapted to provide electrical therapy and/or to provide drug-eluting therapy. One embodiment of the device includes a stent-like structure adapted to be chronically placed intravascularly in the biosystem.

One aspect of the present invention is a system. According to one embodiment, the system includes a planet and at least one satellite device adapted to communicate with the planet. The satellite device includes a structure adapted to be chronically placed within a biosystem, and further includes sensing circuitry and therapy-providing circuitry attached to the structure. The sensing circuitry is adapted to sense mechanical parameters in the biosystem. The therapy-providing circuitry is adapted to provide therapy to the biosystem. In one embodiment, the planet and at least one satellite device communicate wirelessly.

One aspect of the present invention is a method. According to one embodiment, a device is inserted intravascularly, a mechanical parameter is sensed using the device, and therapy is provided using the device. According to one embodiment, an intravascular stent is placed. Hemodynamic parameters are sensed and electrical therapy is provided using the stent. In one embodiment, hemodynamic parameters are sensed and drug-eluting therapy is provided using the stent.

These and other aspects, embodiments, advantages, and features will become apparent from the following description of the invention and the referenced drawings.

DETAILED DESCRIPTION OF THE INVENTION

Figures 1, 2:
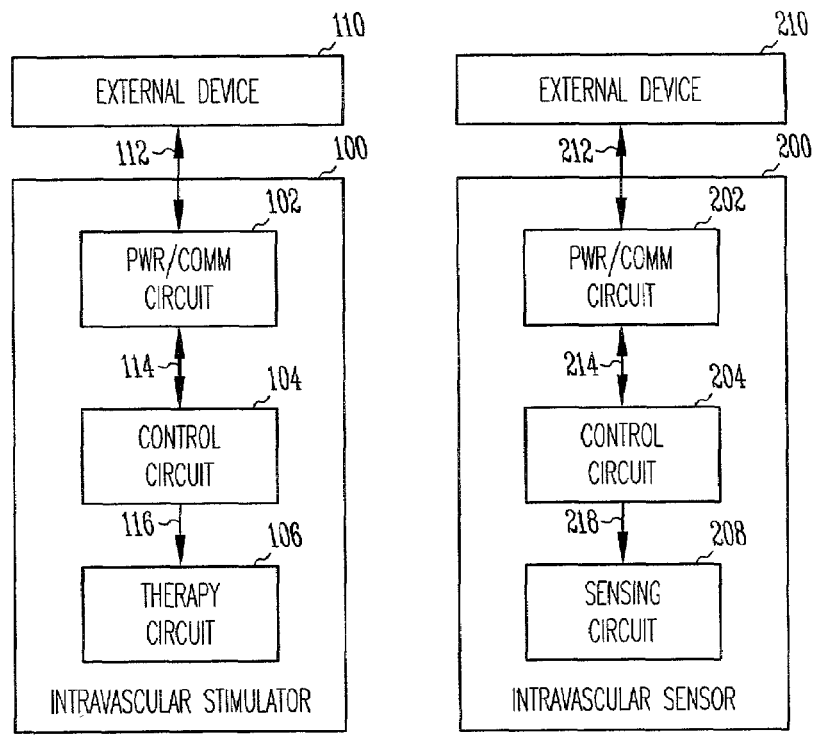
FIG. 1 is a block diagram of one embodiment of a chronically-implanted device.
FIG. 2 is a block diagram of one embodiment of a chronically-implanted device.

The following detailed description of the invention refers to the accompanying drawings which show, by way of illustration, specific aspects and embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. For example, the description herein uses the term "and/or" as in "A, B and/or C, or various combinations thereof." "A, B, and/or C" includes A or B or C, and includes A and B and C. The various combinations of A, B and C includes various combinations of "A", "B" and "C" "AND"ed and "OR"ed together to provide various logical combinations, including A and B, A and C, and B and C. The following detailed description is, therefore, not to be taken in a limiting sense, and the scope of the present invention is defined only by the appended claims, along with the full scope of equivalents to which such claims are entitled.

The present subject matter provides a chronically-implanted device that is capable of sensing events and/or providing therapy. Such sensing includes mechanical, electrical and/or chemical sensing. Such therapy includes mechanical, electrical and/or drug therapy. According to one embodiment, the chronically-implanted device is an intravascular device that is capable of being implanted using a catheter, for example, in a relatively noninvasive procedure.

One embodiment of the chronically-implanted device performs a mechanical function. According to one embodiment, the chronically-implanted device is a stent or otherwise has the functional form of a stent to prevent restenosis, and as such provides a mechanical therapy. Mechanical functions also include, but are not limited to, providing hemodynamic information such as sensed blood pressure and blood flow. Sensing mechanical functions is characterized as one sensing function of the device.

One embodiment of the chronically-implanted device performs an electrical function. According to one embodiment, the chronically-implanted device senses the intrinsic electrical signals of a heart, and provides appropriate electrical therapy in response. According to various embodiments, the appropriate electrical therapy includes pacing pulses and/or defibrillation pulses for a heart. However, the invention is not so limited as the ability to sense electrical signals and/or provide electrical therapy may be desired for other applications.

One embodiment of the chronically-implanted device performs a sensing function. This sensing function includes, but is not limited to, mechanical, electrical and chemical sensing functions.

One embodiment of the chronically-implanted device performs a drug-eluting function. One embodiment of a drug-eluting device dispenses a predetermined amount of a drug at predetermined times. According to one embodiment, the device senses a condition or event for which it is desired to administer a drug, and upon sensing this condition or event, the device appropriately dispenses or elutes the drug to provide the desired therapy. Such conditions or events are mechanically, electrically and /or chemically sensed. One embodiment of a drug-eluting chronically-implanted device is an intravascular device, which elutes a desired drug type and drug dose directly into the blood stream at a desired location upon detection of the condition or event. Such a condition or event includes, but is not limited to, strokes and heart attacks.

One embodiment of the present subject matter provides a unique approach to diagnosing, predicting and/or preventing compromised cardiovascular activity. According to one embodiment, an intravascular device is capable of providing mechanical, electrical and/or chemical sensing capabilities and is further capable of providing mechanical, electrical and/or drug-eluting therapy, or any combination of one or more of these capabilities. According to one embodiment, the intravascular device provides a mechanical function. According to one embodiment, the intravascular device is a stent with sensing, stimulating and drug eluting capabilities, or any combination of one or more of these capabilities.

The following detailed description describes: the chronically-implanted device; the mechanical function of the device including both mechanical therapy and sensing; the electrical function of the device including both electrical therapy and sensing; the various sensing functions of the device in more detail; the drug-eluting or chemical therapy function of the device; a satellite-planet configuration using a plurality of devices; and illustrative applications for the device of the present subject matter. The headings provided within this description are intended to assist the reader, and should not be interpreted to limit the invention. The portions of the description that fall under one heading should not be read in isolation, but rather should be read in context with the remainder of the specification. As such, for example, one embodiment of the chronically-implanted device is capable of performing mechanical and electrical sensing functions, and is capable of performing electrical therapy functions.

Chronically-Implanted Device.

One aspect provides a chronically-implanted device that provides one or more sensing and/or therapy functions. These functions include mechanical, electrical and/or chemical sensing, and further include mechanical, electrical and/or drug-eluting therapy. One embodiment of the chronically-implanted device is an intravascular device. According to various embodiments, the device functions as a sensor, as a stimulator/therapy provider, or as a sensor and stimulator/therapy provider. According to various embodiments, the therapy provided by the device includes electrical stimulus therapy and/or drug therapy. According to various embodiments, sensors and/or simulators are built into and/or onto the structure of the device.

FIG. 1 is a block diagram of one embodiment of a chronically-implanted device. According to this embodiment, the chronically-implanted device 100 forms an intravascular stimulator that includes a power/communication circuit 102, a control circuit 104, and a therapy circuit 106. The therapy circuit 106, generally referred to as a therapy-providing circuit, is operative to provide a desired therapy, such as electrical or drug therapy. Examples of electrical therapy includes pacing and defibrillation pulses. The chronically-implanted device 100 communicates to an external device 10 using communication circuitry within the power/communication circuit 102. The therapy circuit 106, as well as other components of the chronically-implanted device 100, will be described in more detail below.

In one embodiment of the device, the communication link 112 between the external device 110 and the power/communication circuit 102 is bidirectional, the communication link 114 between the power/communication circuit 102 and the control circuit 104 is bidirectional, and the communication link 116 between the control circuit 104 and the therapy circuit 106 needs only to be unidirectional as the control circuit 104 only needs to provide commands to the therapy circuit 106.

In the embodiment illustrated in FIG. 1, the power and communication circuitry 102 are combined into one box to illustrate that they are capable of being integrated. Alternatively, the power circuitry and communication circuitry are capable of being separate circuits. With respect to an integrated power/communication circuit, data is capable of being encoded into the power transmission as a modulation of the power signal. As such, one embodiment of the chronically-implanted device 100 provides a combined power/communication link 112 between the power/communication circuit 102 and the external device 110. Another embodiment of the chronically-implanted device 100 provides a power link and a separate communication link between the power/communication circuit 102 and the external device 110.

One embodiment of the chronically-implanted device 100 provides a wired, combined power/communication link and another embodiment provides a wireless, combined power/communication link. Furthermore, with respect to device embodiments that include separate power and communication links, the power link is capable of being either wired or wireless, and the communication link is independently capable of being either wired or wireless.

FIG. 2 is a block diagram of one embodiment of a chronically-implanted device. According to this embodiment, the chronically-implanted device 200 forms an intravascular sensor that includes a power/communication circuit 202, a control circuit 204, and a sensing circuit 208. According to various embodiments, the sensing circuit 208 is operative to sense various events such as mechanical, electrical and chemical events. The sensing circuit 208, as well as the other components of the chronically-implanted device, will be described in more detail below.

In one embodiment, the communication link 212 between the external device 210 and the power/communication circuit 202 is bidirectional, the communication link 214 between the power/communication circuit 202 and the control circuit 204 is bidirectional, and the communication link 218 between the control circuit 204 and the sensing circuit 208 is bidirectional as the control circuit 204 communicates with the sensing circuit 208 and the sensing circuit 208 communicates sensed data to the control circuit 204.

In the embodiment illustrated in FIG. 2, the power and communication circuitry 202 are combined into one box to illustrate that they are capable of being integrated. Alternatively, the power circuitry and communication circuitry are capable of being separate circuits. With respect to an integrated power/communication circuit, data is capable of being encoded into the power transmission as a modulation of the power signal. As such, one embodiment of the chronically-implanted device 200 provides a combined power/communication link 212 between the power/communication circuit 202 and the external device 210. Another embodiment of the chronically-implanted device 200 provides a power link and a separate communication link between the power/communication circuit 202 and the external device 210.

One embodiment of the chronically-implanted device 200 provides a wired, combined power/communication link and another embodiment provides a wireless, combined power/communication link. Furthermore, with respect to device embodiments that include separate power and communication links, the power link is capable of being either wired or wireless, and the communication link is independently capable of being either wired or wireless.

Figure 3:
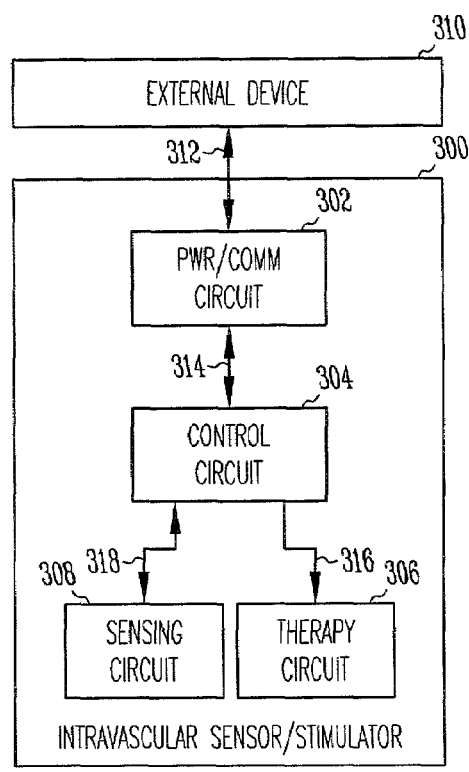
FIG. 3 is a block diagram of one embodiment of a chronically-implanted device.

FIG. 3 is a block diagram of one embodiment of a chronically-implanted device. According to this embodiment, the chronically-implanted device 300 forms an intravascular sensor/stimulator that includes a power/communication circuit 302, a control circuit 304, a therapy circuit 306, and a sensing circuit 308. The components of the chronically-implanted device 300 will be described in more detail below. The therapy circuit 306 functions as a therapy-providing circuit which is operative to provide the desired therapy, such as electrical or drug therapy. The sensing circuit 308 is operative to sense various events such as mechanical, electrical and chemical events.

According to one embodiment, the communication link 312 between the external device 310 and the power/communication circuit 302 is bidirectional, the communication link 314 between the power/communication circuit 302 and the control circuit 304 is bidirectional, the communication link 316 between the control circuit 304 and the therapy circuit 306 is unidirectional as the control circuit 304 provides commands to the therapy circuit 306, and the communication link 318 between the control circuit 304 and the sensing circuit 308 is bidirectional as the control circuit 304 communicates with the sensing circuit 308 and the sensing circuit 308 communicates sensed data to the control circuit 304.

In the embodiment of FIG. 3, the power and communication circuitry 302 are combined into one box to illustrate that they are capable of being integrated. Alternatively, the power circuitry and communication circuitry are capable of being separate circuits. With respect to an integrated power/communication circuit, data is capable of being encoded into the power transmission as a modulation of the power signal. As such, one embodiment of the chronically-implanted device 300 provides a combined power/communication link 312 between the power/communication circuit 302 and the external device 310. Another embodiment of the chronically-implanted device 300 provides a power link and a separate communication link between the power/communication circuit 302 and the external device 310. One embodiment of the chronically-implanted device 300 provides a wired, combined power/communication link and another embodiment includes a wireless, combined power/communication link. Furthermore, with respect to device embodiments that include separate power and communication links, the power link is capable of being either wired or wireless, and the communication link is independently capable of being either wired or wireless.

According to one embodiment, the chronically-implanted device is an intravascular device. According to one embodiment, the chronically-implanted device has the form of a stent or a stent-like device that is capable of performing at least some, if not all, of the functions of a stent. According to various embodiments, the device functions as a satellite and communicates to the planet by way of dedicated data and/or power lines, a single wire connection such that it functions as a second tip, or through some non-physical means such as RF or ultrasound energy. The satellite-planet configuration will be described in more detail below.

MEMS Technology.

According to various embodiments, Micro-Electro-Mechanical Systems (MEMS) technology is used to fabricate the required circuitry for the chronically-implanted device on silicon substrate. Currently, for example, the MEMS circuitry is between about 1 mm×3 mm for some of the present applications; however, the MEMS circuitry is capable of being otherwise sized. MEMS devices have been used in catheter-based systems to measure intracardiac pressure and temperature.

In general, a MEMS device contains micro-circuitry on a tiny silicon chip into which some mechanical device such as a sensor has been manufactured. These chips are able to be built in large quantities at low cost, making the MEMS device cost-effective. MEMS technology integrates mechanical elements, sensors, actuators, and electronics on a common silicon substrate using microfabrication technology. MEMS combines silicon-based microelectronics with microsensors and microactuators to provide a complete system on a chip. The micromechanical components are fabricated using micromachining processes that are compatible with the integrated circuit process sequences. Parts of the silicon wafer are selectively etched away or new structural layers are added to form the mechanical and electromechanical devices. According to various embodiments of the chronically-implanted device, at least one of the components (i.e. the power circuitry, the communication circuitry, the control circuitry, the stimulation circuitry, and the sensing circuitry) are integrated onto silicon MEMS technology to reduce size.

Communication.

The chronically-implanted device includes communication circuitry used to communicate to an external device. According to various embodiments, for example, the communication circuitry forms part of the power/communication circuits 102, 202 and 302 of FIGS. 1–3. One example of an external device is a cardiac stimulus device, such as an implantable pacemaker or ICD. Another example of external device is a planet in a satellite-planet system, which will be described in more detail below. According to various embodiments, the chronically-implanted device communicates to the external device through wire and wireless mediums.

In one embodiment, a small lead tethers the chronically-implanted device to the external device. Other embodiments provide communication between the chronically-implanted device and the external device using radio-frequency (RF) waves, for example.

Figure 4:
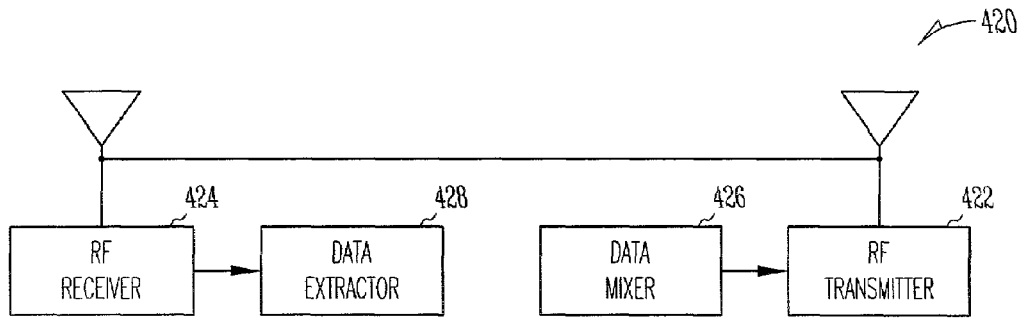
FIG. 4 illustrates one embodiment of RF power/communication circuitry for a chronically-implanted device.

FIG. 4 illustrates one embodiment of power/communication circuitry for a chronically-implanted device in which the power/communication circuitry includes RF circuitry. One embodiment of the RF circuitry 420 includes an RF transmitter 422 to transmit RF energy to an external device and/or an RF receiver 424 to receive RF energy from an external device. The illustrated RF circuitry 420 includes a data mixer 426 to encode data in preparation for the transmission of the data to the external device using the RF transmitter 422, and a data extractor 428 to decode data upon receiving a data transmission from the external device using the RF receiver. The external device includes similar circuitry to communicate with the chronically-implanted device. With the RF circuitry, one embodiment of the chronically-implanted device is capable of sending and/or receiving data via RF energy, and one embodiment is capable of sending and/or receiving data and is capable of receiving power via RF energy.

The communication may be either uni-directional or bi-directional communication. In one RF communication embodiment, the chronically-implanted device itself functions as the antenna/coil. For example, the wire(s) that form a stent-like device function as the antenna.

One embodiment of the chronically-implanted device communicates through an electric field, and includes a communications component joined by an electrically split stent operably connected to the communications component that includes a receiver, a transmitter or both. The receiver detects differential signals within a pass band using the electrically split stent and present the detected signal to the computation component. The transmitter differentially drives the electrically split stent to provide an electric field to carry data. An implanted microsystem is able to communicate through an electric field, and an external control system is able to communicate to the implanted device, such as through body contact or body proximity. One example involves differential capacitive coupling for receiving and/or transmitting. One-way broadcasts are used in less reliable data transfers, and two-way broadcasts are used in more reliable transfers where receipt of a data packet is acknowledged. An intermediate communication node is incorporated, as desired or needed, to provide a repeater function to extend the communication reach of remote devices.

The split stent is formed by splitting a metal stent. According to one embodiment, the metal stent is split radially. According to another embodiment, the metal stent is split longitudinally. According to another embodiment, the metal stent is split in a spiral. The stent may be split either symmetrically or asymmetrically. The split stent is mechanically re-joined using an electrically insulating medium, and the split portions of the stent are electrically connected to a microsystem containing an integrated electronic communications device capable of differentially driving the stent halves and/or receiving differential signals from the stent halves. According to one embodiment, the microsystem is mechanically attached to the stent structure such that the microsystem resists being detached from the stent during stent expansion. Additionally, according to this embodiment, the microsystem is longitudinally conformal to the stent to streamline vascular emplacement.

In one embodiment, the communication or power/communication circuit uses ultrasonic energy. Ultrasonic circuitry is not explicitly shown. One of ordinary skill in the art will understand, upon reading and comprehending this disclosure, how to incorporate ultrasonic circuitry in the chronically-implanted device.

Power.

The chronically-implanted device includes power circuitry. According to various embodiments, for example, the power circuitry forms part of the power/communication circuits 102, 202 and 302 of FIGS. 1–3. According to various embodiments, the chronically-implanted device is powered by a small battery, is powered by a separate control unit (CU), such as an external device, through a small lead tethering the intravascular device to the CU, is powered by the CU wirelessly by RF transmissions, magnetic induction power transmissions or ultrasonic waves, and/or is powered by a biofuel cell which is described in more detail below. One embodiment of an RF circuit 420 was illustrated in FIG. 4 and was described above with respect to Communications, and as such, will not be repeated here. With the RF circuitry, one embodiment is capable of receiving power via RF energy; and one embodiment is capable of sending and/or receiving data and is capable of receiving power via RF energy.

The power circuitry provides power to all other functional circuits of the system. According to one embodiment, the power circuitry is designed to selectively gate power to certain system components on demand or upon receiving a command signal, thus conserving the amount of energy consumed by the device. In one embodiment, the power circuitry is adapted to convert RF energy to charge and to store the charge in a charge-storing device such as a capacitor, rechargeable battery and the like. According to one embodiment, the power circuitry has one or more storage capacitors for storing charge as necessary to power the circuit between RF transmissions. One embodiment of the device integrates the charge storage capacitor into silicon, and another embodiment provides a charge storage capacitor that is a discrete component. According to one embodiment for RF or magnetic induction powering, the chronically-implanted device employs a charging circuit, storage capacitors, and a voltage regulator circuit to supply power between RF transmissions.

One embodiment of the chronically-implanted device includes a power circuit that employs a biofuel cell to generate electrical power in a non-self-contained process within a biological system, which as a result, permits significantly smaller component sizes. For example, about 50% of the volume of a presently implanted pacemaker is dedicated to a battery. Thus, by eliminating a battery and using reactants available within the biosystem, the biofuel cell allows the design of the device to be further miniaturized. Smaller designs are able to be placed using relatively noninvasive procedures such as through a hypodermic needle or intravascularly using a catheter. Additionally, smaller designs are able to be placed in more positions. Furthermore, for a given device size, miniaturization allows more functions to be included on a device.

One embodiment employs a split stent-like structure to power miniature electronic systems, or Microsystems, which are vascularly implanted in a biosystem using minimally invasive techniques. These minimally invasive techniques include, for example, emplacement using a needle delivery system or balloon catheter.

According to one embodiment, the stent-like biofuel cell power generator is physically separated from a biocompatible microsystem, i.e. from the chronically-implanted device. Wiring connects the power generator to the microsystem. It is desired that the wiring be insulated, highly flexure compliant, and biocompatible similar to modern cardiac lead technology. The term flexure compliant denotes a flexible element, but with low occurrence of flex-induced breakage.

According to one embodiment, the stent-like biofuel cell power generator is physically co-located and mechanically attached or bonded to the biocompatible microsystem, i.e. to the chronically-implanted device. The electrical connection between the power generator and the microsystem is integrated into the bonding or the conformal microsystem insertion protection structure and is comprised of biocompatible materials such as those used in modem cardiac lead technology.

The power required for the microsystem circuitry for the chronically-implanted device is able to be generated remotely using the biofuel cell power generator technology. Accordingly, applications are able to be performed more remotely as they do not need to be powered by a separate device. According to one embodiment, the biofuel cell power generator is positioned down-stream from the microsystem so as to minimize contamination from fuel cell waste products.

Control.

According to one embodiment, the chronically-implanted device includes control circuitry 104, 204 and 304 to control the functions of one or more of the subsystems or components shown in FIGS. 1–3. According to various embodiments, the chronically-implanted device employs a dedicated controller to monitor, to control, or to monitor and control the functions of any or all of the components shown in FIGS. 1–3.

According to various embodiments, the controller is adapted to trigger the sensing circuit, the stimulating circuit, or the sensing and stimulating circuits. According to one embodiment, the controller is used to manage system power by controlling power flow between the power circuitry and other system components. The controller is capable of controlling the operation of any system component, and of providing the system clock for electronics timing and functionality. According to one embodiment, the controller is a state machine.

According to one satellite-planet embodiment, which will be described in more detail below, the controller is configured to operate when triggered by the planet. According to one embodiment, the controller is used to decode detected data/commands from the planet.

According to one embodiment, the controller is capable of controlling any one or more of the above-described subsystems or components shown in FIGS. 1–3, or any combination thereof. According to one embodiment, the controller is capable of controlling all of the subsystems.

Sensing.

Figure 5:
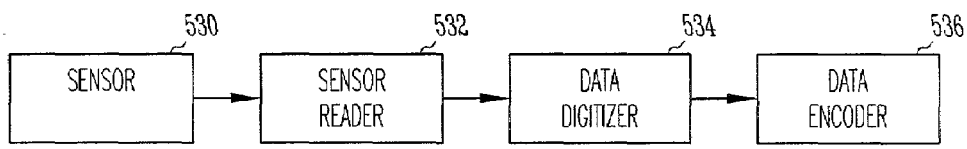
FIG. 5 illustrates one embodiment of sensing circuitry for a chronically-implanted device.

FIG. 5 illustrates one embodiment of sensing circuitry for a chronically-implanted device. Such sensing circuitry includes the sensing circuitry 208 and 308 of FIGS. 2 and 3. In one embodiment, the sensing circuitry 508 includes a sensor 530, a sensor reader 532, a data digitizer 534, and a data encoder 536. As will be discussed in detail below with respect to the sensing functions of the chronically-implanted device, the sensor 530 is able to take many forms. The sensor reader 532 functions as interface circuitry to the sensor 530, such as a voltage measuring circuit for a potentiometric sensor and a current measuring circuit for an amperometric sensor. The data digitizer 534 is used if the sensor data is to be sent using a digital communication medium. The digital data includes ones and zeros, and also includes variants such as pulse width modulation (PWM) for an RF transmission.

According to one embodiment, the data encoder 536 encodes the data into a simple, compact and efficient form for transmission.

According to one embodiment, the sensing circuitry is adapted to sense electrophysiological properties of local tissue. In one embodiment, the entire or at least part of the chronically-implanted device functions as the stimulating electrode(s). According to various embodiments, the sensing circuitry includes one or various combinations of the following sensors: a capacitive membrane sensor, a piezoresistive sensor, an impedance sensor, an ion-selective sensor, an oxygen sensor, and a biosensor.

According to various embodiments, the capacitive membrane sensor is used to measure pressure within the vessel wall, to derive flow, to derive rate, to monitor cardiac output, to monitor hemodynamic stability, and to monitor Electro-Mechanical Dissociation (EMD). It was stated earlier in the background that there is a correlation between cardiac electrical abnormalities and coronary vascular abnormalities. However, it is possible that the electrical functions appear normal but the mechanical functions are abnormal, or that the mechanical functions are normal but the electrical functions appear abnormal. EMD identifies conditions in which electrical and mechanical functions of the biological system are not in accord or agreement with each other.

According to various embodiments, the piezoresistive sensor is used to measure pressure within the vessel wall, to derive flow, to derive rate, to monitor cardiac output, to monitor hemodynamic stability, and to monitor EMD. In one embodiment the piezoresistive sensor is used to measure contraction strength of the heart.

According to various embodiments, the impedance sensor is used to monitor vessel inner diameter, and used as a traditional intracardiac impedance sensor to inject current, measure voltage, and calculate resistance. According to this embodiment, the vessel inner diameter is derived as a function of the resistance and assumes a relatively fixed blood resistivity. According to one embodiment, should coagulation and/or fibrosis corrupt the signal from the impedance sensor over time, the corruption of the impedance sensor signals is used to provide a measure of the coagulation and/or the fibrosis on, or near, the intravascular device.

According to various embodiments, the ion-selective sensor is used to monitor the level of given ions within the bloodstream. Examples of monitored ions include oxygen, potassium, sodium, drug-influenced ions, and (re)stenosis-influenced ions.

According to various embodiments, the oxygen sensor is used to provide feedback for rate-adaptive pacing and/or hemodynamic information on tachycardia. According to one embodiment, should coagulation and/or fibrosis corrupt the signal from the oxygen sensor over time, the corruption of the oxygen sensor signal is used to measure coagulation and/or fibrosis on, or near, the intravascular device.

According to various embodiments, the biosensor is used to monitor the level of given hormones in the bloodstream. According to this embodiment, the hormones that are known to affect cardiac output can be monitored to assess the effects of the autonomic nervous system on cardiac function. Examples of monitored hormones include epinephrine and norepinephrine.

According to various embodiments, the biosensor is used to monitor the level of given enzymes in the bloodstream. According to this embodiment, the enzymes that are known to be released immediately after a myocardial infarction can be monitored to determined if a myocardial infarction occurred. Examples of monitored enzymes include creatine phosphokinase (CPK) and lactate dehydrogenase (LDH).

Stimulating.

According to various embodiments, the therapy circuitry 606 is adapted for providing therapy. Such therapy circuitry includes the therapy circuitry 206 and 306 of FIGS. 2 and 3. In one embodiment, the entire or at least part of the intravascular device functions as the stimulating electrode(s). The stimulating circuitry, also referred to as therapy-providing circuitry, includes circuitry for providing electrical therapy and drug-eluting therapy.

Figure 6:
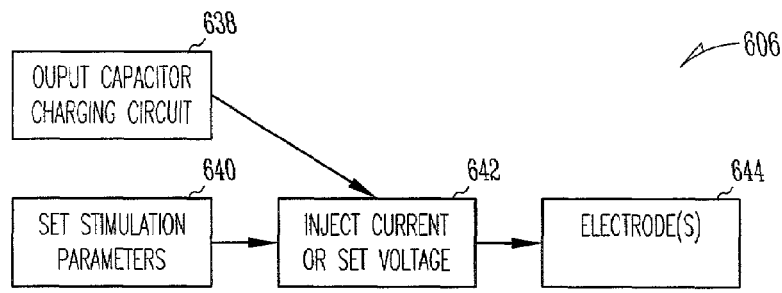
FIG. 6 illustrates one embodiment of stimulating circuitry for a chronically-implanted device.

FIG. 6 illustrates one embodiment of stimulating circuitry for a chronically-implanted device. According to one embodiment, the therapy circuitry 606 includes an output capacitor charging circuit 638, a set stimulation parameters circuit 640, an inject current or set voltage circuit 642, and electrodes 644.

According to one embodiment, the output capacitor charging circuit 638 is capable of energy sourcing from capacitors and/or inductors. According to various embodiments, the output capacitor charging circuit 638 is charged either from the power circuitry or directly from the RF signal.

According to one embodiment, the set stimulation parameters circuit 640 is used to adjust stimulation parameters such as pulse width, amplitude stimulation modes (bi-polar or uni-polar, for example), and stimulation site if multiple sites are available. According to one embodiment, the therapy circuitry 606 receives its parameters from the controller.

The inject current or set voltage circuit 642 is the output stage for the stimulus and includes any necessary protection circuits such as diodes and DC blocking caps. According to one embodiment, the inject current or set voltage circuit accommodates various stimulation wave forms such as biphasic, monophasic, subthreshold, and pulse timing.

The electrodes 644 are the output stage device. According to various embodiments, the electrodes are the chronically-implanted device itself or selected portions thereof, or are separate devices.

Mechanical Function.

As used herein, the term mechanical function includes both the exertion of mechanical forces by the device and the detection or sensing of mechanical forces by the device. For example, in the embodiment in which the chronically-implanted device has a stent-like form, the structure of the expanded device exerts a pressure on vascular walls to prevent restenosis. Additionally, various embodiments of the chronically-implanted device includes appropriate sensors for monitoring mechanical/fluid properties such as the hemodynamic properties of blood flow and pressure. The sensing function is described in more detail below. Furthermore, one embodiment of the chronically-implanted device has the structure of and performs the mechanical function of a vascular occlusion device.

The American Heart Association estimates that 70–90% of balloon angioplasty procedures involve the placement of a stent. The present subject matter takes advantage of the prevalence of stents, and the relatively non-invasive procedure for placing the stents. The primary purpose of these stents is to prevent restenosis of the arteries. According to one embodiment, the chronically-implanted device performs the mechanical function of a stent to prevent restenosis, and forms an intelligent stent that provides other functions beyond that provided by a conventional stent. That is, one embodiment of the device is a stent that is capable of performing intravascular sensing, such as mechanical, electrical and/or chemical sensing, and is further capable of performing electrical and/or drug eluting therapies.

Figure 7:
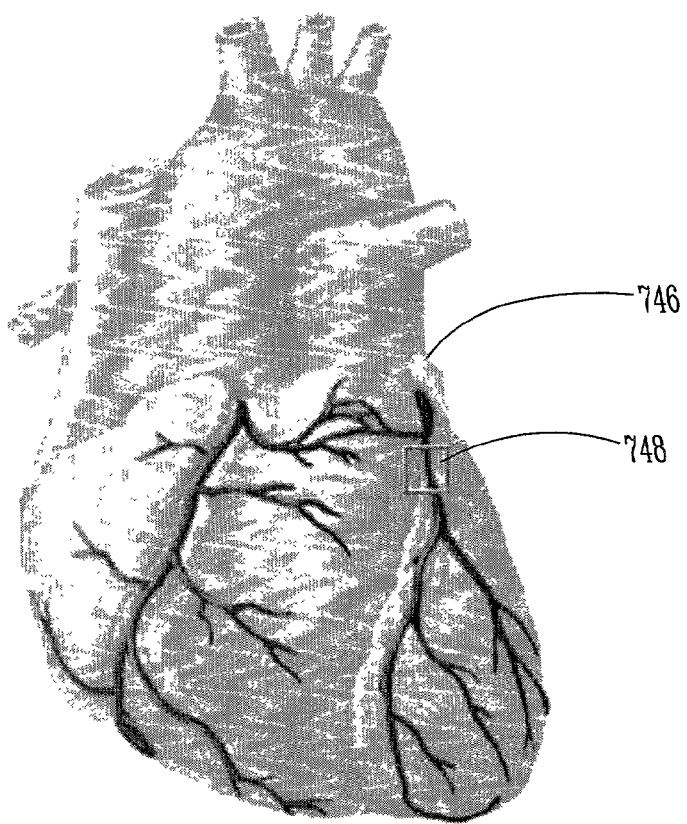
FIG. 7 illustrates a heart, and provides an example of a location where a coronary stent may be placed within a coronary vessel.
Figure 8:
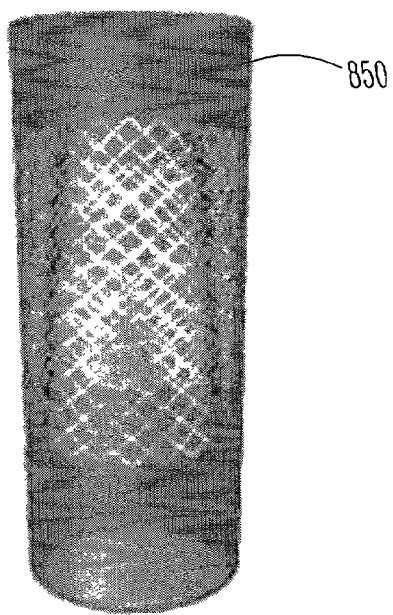
FIG. 8 illustrates a wire mesh stent that may be placed in a coronary vessel.
Figure 9:
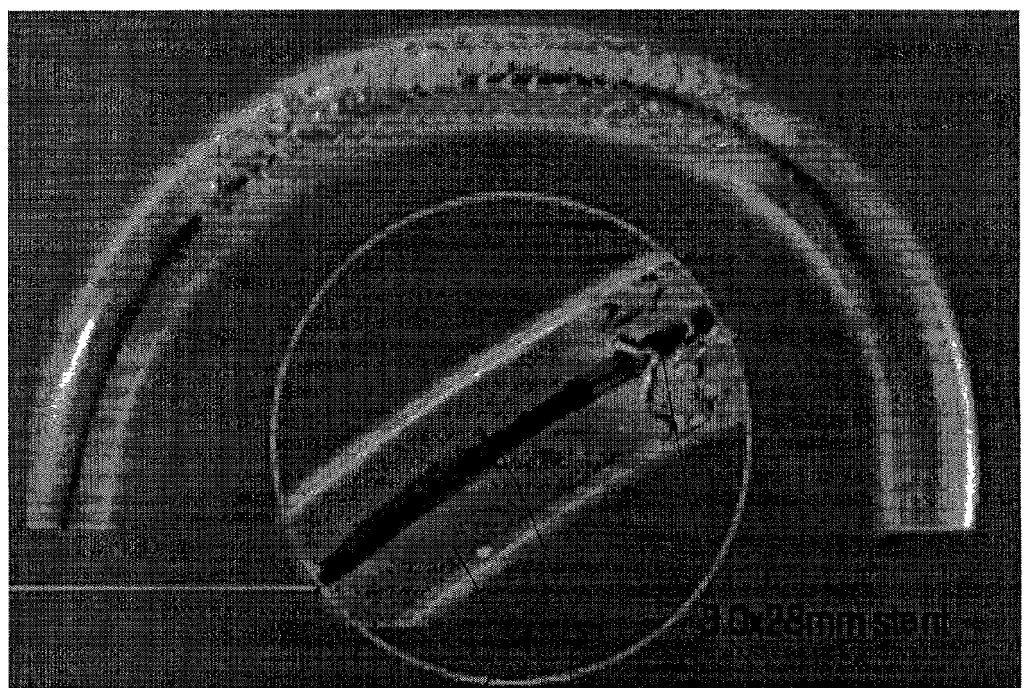
FIG. 9 illustrates a stent placement within a vessel using a catheter.

FIG. 7 illustrates a heart 746, and provides an example of a location where a coronary stent may be placed within a coronary vessel. Should the portion of the vessel identified by the square 748 narrows, a stent is able to be placed within this portion of the vessel and expanded to widen the lumen of that portion of the vessel. FIG. 8 illustrates a wire mesh stent 850 that may be placed in a coronary vessel such as that shown in FIG. 7. FIG. 9 illustrates a stent placement within a vessel using a catheter. The catheter 952 moves the stent 950 into the desired place within the vessel 954, and then opens or expands the stent 950.

Embodiments of the stent-like, chronically-implanted device include balloon-expandable stents and self-expanding stents. The expanded stent applies pressure against the interior of the vessel to widen the vessel. The catheter is removed, leaving the expanded stent securely in place.

Figure 10:
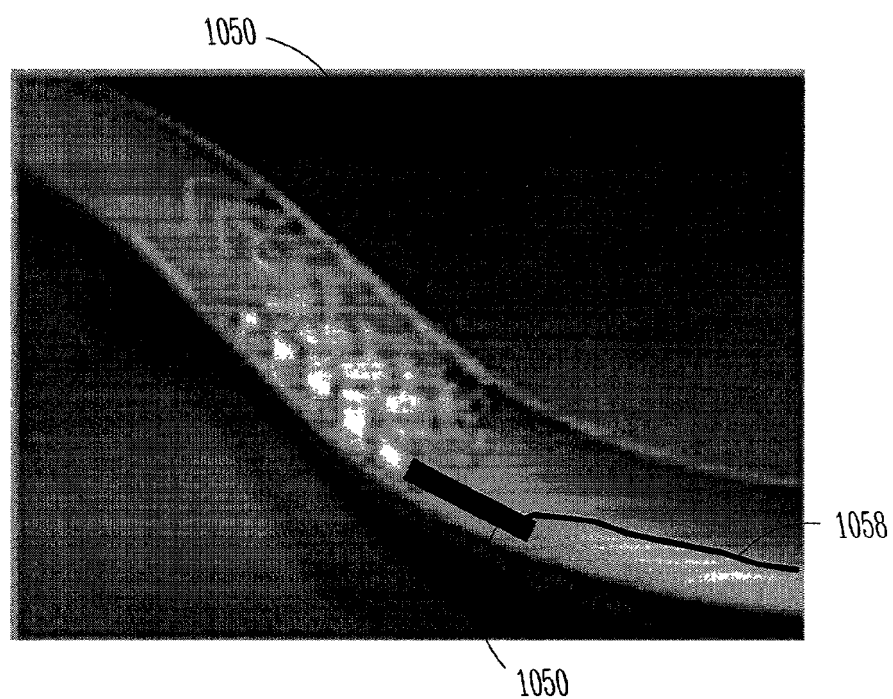
FIG. 10 illustrates a chronically-implanted device in the form of a stent placed within a vessel in which the device includes an encapsulated electronics platform and an optional power/communication tether.

FIG. 10 illustrates a chronically-implanted device in the form of a stent 1050 placed within a vessel in which the device includes an encapsulated electronics platform 1056 and an optional power/communication tether 1058. Intelligent functions, in addition to the mechanical function of preventing restenosis, are capable of being performed by the stent because of circuitry, or Microsystems, contained on the electronics platform 1056 and the power/communication tether 1058.

The chronically-implanted device diminishes problems associated with invasive surgical procedures because the device is small and is capable of being placed by a hypodermic needle or a catheter, for example, into position through the vascular network or through the lumen of other canals or tubular structures of a biosystem. Additionally, in the embodiment in which the intravascular device performs the mechanical function of a stent to prevent stenosis or restenosis, the intravascular device performs the function of the stent and further performs intelligent functions without requiring additional invasive procedures.

According to various embodiments, the chronically-implanted device of the present subject matter may be formed to function as a variety of stents. In addition to the above described coronary stent, these stents include, but are not limited to, a vascular stent, a tracheobronchial stent, a colonic/duodenal stent, a esophageal stent, a biliary stent, a urological stent, a neurovascular stent, an abdominal aortic aneurysm stent, a renal stent, and a carotid stent. These stents are briefly described below.

A vascular stent, for example, is used to maintain blood flow through the femoral artery in the thigh and the poplitial artery behind the knee. One example of vascular stent is the Medtronic VasculCoil® device.

A tracheobronchial stent, for example, is used to maintain the air passageway when partially obstructed by a malignant growth. One example of a tracheobronchial stent is the Boston Scientific Wallstent® device.

A colonic/duodenal stent, for example, is used to maintain the digestive passageway when partially obstructed by a malignant growth or constriction. An example of a colonic/duodenal stent is the Boston Scientific Wallstent® device.

An esophageal stent, for example, is used to maintain the food passageway when partially obstructed by a malignant growth. Examples of an esophageal stent include the Boston Scientific Ultraflex™ device and the Medtronic EsophaCoil® device.

A biliary stent, for example, is used to maintain patency of the duct that carries bile from the liver to the gall bladder. Examples of a biliary stent include the Guidant Herculink™, Megalink™ and Dynalink™ devices, the Boston Scientific Symphony® device, the Cordis Precise™ and SMART™ devices, and the Medtronic EndoCoil® device.

A urological stent, for example, is used in the treatment of strictures of the male urethra. Such urological stents include the Boston Scientific Percuflex® and Beamer™ devices, and the Medtronic UroCoil® device. Urological stents are also used in the treatment of urethral obstructions caused by the enlargement of the prostrate gland. Such urological stents include the Medtronic ProstaCoil®.

A neurovascular stent, for example, is used in the treatment of atherosclerotic disease deep within the brain. One example of a neurovascular stent is the Medtronic INX™ device.

An abdominal aortic aneurysm stent, for example, is used in the treatment of abdominal aortic aneurysms. Examples of abdominal aortic aneurysm stents include the Guidant Ancure™ device and the Medtronic AneuRx™ device.

A renal stent, for example, is used in the treatment of atherosclerotic disease in the renal arteries. One example of a renal stent is the Medtronic Bridge X3™ device.

A carotid stent, for example, is used in the treatment of atherosclerotic disease in the carotid arteries. Medtronic provides one example of a carotid stent.

As one of ordinary skill in the art will understand upon reading and comprehending this disclosure, the chronically-implanted device of the present subject matter is capable of being formed to perform the mechanical function of any of the above-described stents, and is capable of being designed to provide the desired mechanical, electrical and/or chemical sensing, and/or the desired electrical and/or drug-eluting therapy for a desired application. For example, the carotid stent is a useful place to monitor pressures or flow because of the implications it would have for brain perfusion and presumably consciousness. It could be used not only for prediction of events but also for defibrillation therapy in terms of determining what rhythms were hemodynamically stable vs. unstable.

According to one aspect of the present invention, the chronically-implanted devices are used as coronary artery stents that function as arterial-based ischemic detectors for sensing constriction and/or closure of the vessels. Coronary artery disease (CAD) is prevalent among ICD patients, and may lead to ischemic episodes that precipitate VT/VF. One promising strategy for predicting certain VT/VF events and applying preventive therapy includes sensing these ischemic episodes. Stents are placed in vessels that have already exhibited levels of occlusion and are likely to exhibit future occlusion. According to one embodiment, detecting these changes provides a warning of ischemic onset independently or in conjunction with electrogram morphology. According to one embodiment, the resonance of the metal stents following an acoustic input depends on the surrounding blockage and/or blood flow.

Figure 11:
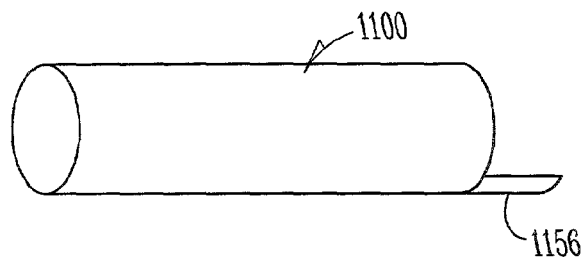
FIG. 11 illustrates one embodiment of a chronically-implanted device in the form of a stent that includes an encapsulated electronics platform.
Figure 12:
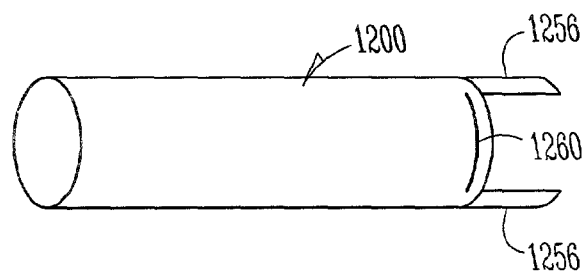
FIG. 12 illustrates one embodiment of a chronically-implanted device in the form of a stent that includes two encapsulated electronics platforms.

FIG. 11 illustrates one embodiment of a chronically-implanted device 1100 in the form of a stent that includes an encapsulated electronics platform 1156. The electronics platform 1156 includes the circuitry from the various embodiments previously shown and described with respect to FIGS. 1–3. FIG. 12 illustrates one embodiment of a chronically-implanted device 1200 in the form of a stent that includes two encapsulated electronics platforms 1256. Additional electronic platforms may be incorporated as desired. One embodiment of the device includes at least one dedicated electrical connector that couples two or more electronics platforms. One embodiment of the device uses an insulated strand of mesh 1260 from the stent structure to couple two or more electronics platforms.

The stent-like structure of one chronically-implanted device includes at least two conducting portions separated by an insulator. One of the conducting portions functions as an anode and another functions as a cathode. These conducting portions are used, according to various embodiments of the chronically-implanted device, to provide electrical therapy, to receive power transmissions, and/or to receive and transmit communication transmissions.

Figure 13:
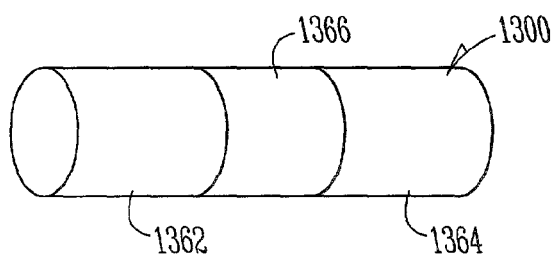
FIG. 13 illustrates one embodiment of a chronically-implanted device having a cylindrical or radially-oriented anode and cathode.
Figure 14:
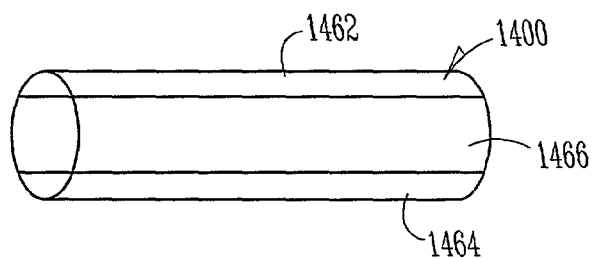
FIG. 14 illustrates one embodiment of a chronically-implanted device having a longitudinally-oriented anode and cathode.

FIG. 13 illustrates one embodiment of a chronically-implanted device 1300 having a cylindrical or radially-oriented anode 1362 and cathode 1364. FIG. 14 illustrates one embodiment of a chronically-implanted device 1400 having a longitudinally-oriented anode 1462 and cathode 1464. According to various embodiments, these split stent-like structures are formed from a conventional stent. The conventional stent is cut as required to form or isolate a radially-oriented anode and cathode or a longitudinally-oriented anode and cathode. The anode and cathode are recombined using an insulator material 1366 or 1466.

Electrical Function.

As used herein, the term electrical function includes electrical therapy such as that provided for pacing or defibrillating purposes, and electrical sensing such as that for sensing cardiac arrhythmias. According to one embodiment, a chronically-implanted device, such as an intravascular stent-like device, is placed in a coronary artery using a relatively noninvasive procedure to deliver electrical stimuli as part of a pacing function and/or defibrillation function and/or arrhythmia prevention. According to one embodiment, a plurality of chronically-implanted devices are placed in coronary arteries to deliver electrical pacing stimuli as part of a multisite pacing system. Multisite pacing has been proposed for the purpose of improving cardiac mechanical function, improving antitachycardia pacing (ATP) strategies, and providing preventive pacing schemes. However, traditional technologies for pacing have been limited to intracavitary catheters, transvenous leads, or screw-in button electrodes. The intravascular, chronically-implanted device is capable of being placed in any blood vessels, including arteries, because of its small size. Thus, additional therapy strategies are available.

A power supply is required to provide the electrical therapy, such as pacing and defibrillation pulses. According to one embodiment, a battery is incorporated within a stent. According to one embodiment, stents are acoustically triggered to deliver electrical therapy. According to other embodiments, a resonance is created to mechanically induce stimulation, or an applied signal polarizes the stent and a "break" excitation occurs after turning the signal off. According to other embodiments, biofuel cells are used to generate the power for the electrical therapy.

Multi-site pacing using the chronically-implanted devices, particularly the intravascular stent-like device, provides a number of possibilities for electrical vectors between two or more chronically-implanted devices in a device-to-device electrical configuration, and between at least one chronically-implanted device and an external device or devices, such as a CAN of a pacemaker, in a device-to-can electrical configuration. Electrical vectors include both the magnitude and polarity of electrical pulses. According to various embodiments, the number and locality of the chronically-implanted devices are chosen so as to be able to reduce the magnitude of the electrical pulses and still provide effective, electrical therapy.

Sensing Function.

Various embodiments of the chronically-implanted device include sensors, as well as associated circuitry for performing analysis on sensed data, that are capable of sensing one or more mechanical events or conditions, one or more electrical events or conditions, and/or one or more chemical events or conditions. Sensors, as categorized by transducer type, include pressure-based sensors such as piezoelectric crystals and capacitive membrane sensors, electrical-based sensors such as potentiometric and amperometric sensors, electrical-chemical based sensors, biochemical-based sensors, magnetic-based sensors, temperature-based sensors, mechanical-based sensors, gravimetric or accelerometer sensors, and optical-based sensors such as oxygen sensors for measuring oxygen saturation or percent oxygen. The following provides examples of sensors. These examples are not intended to be an exclusive listing, and as such should not be read to limit the type of sensors encompassed in the present subject matter.

Figure 15:
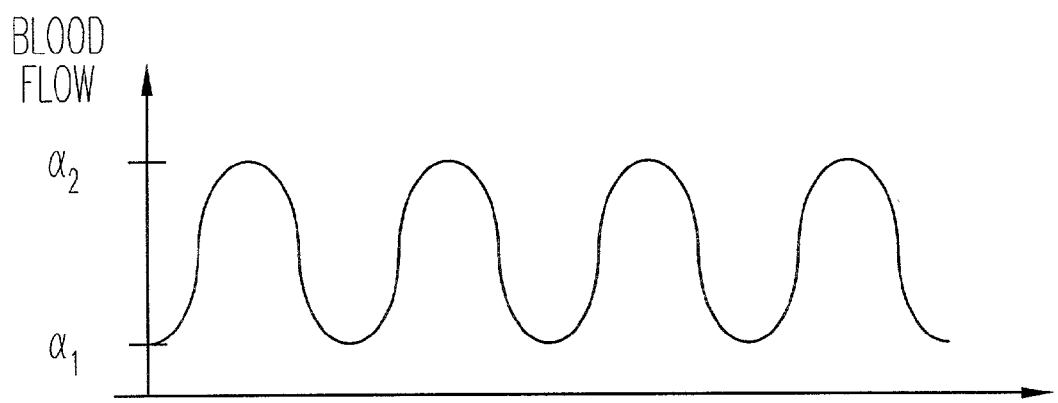
FIG. 15 is a graph illustrating blood flow as derived from time and sensor readings of pressure.
Figure 16:
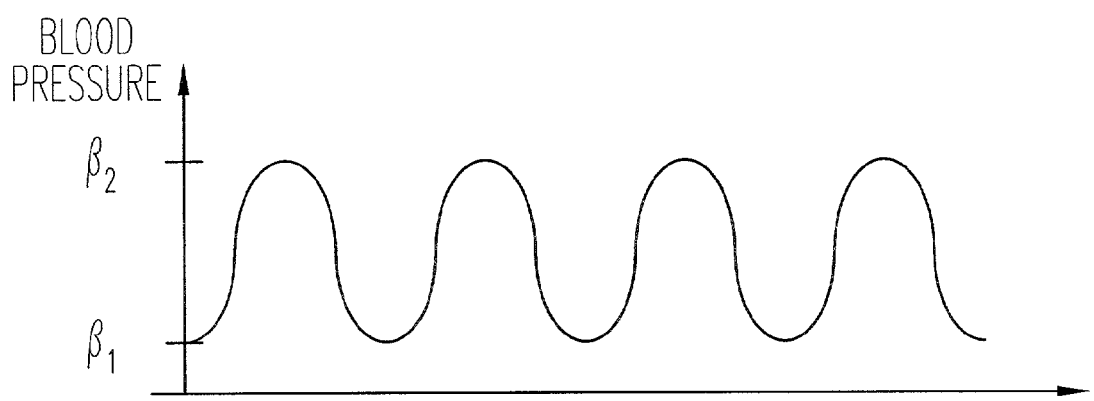
FIG. 16 is a graph illustrating blood pressure as determined by sensor readings.
Figure 17:
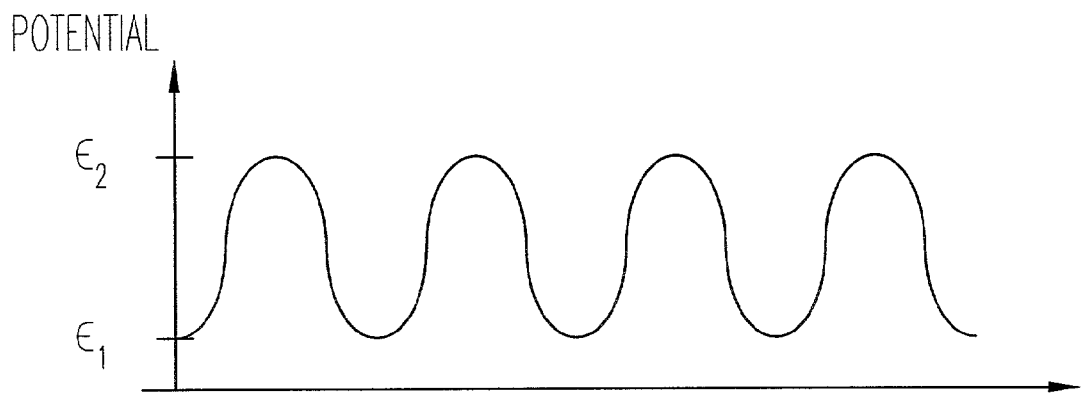
FIG. 17 is a graph illustrating electric potential as determined by sensor readings, which corresponds to blood flow and blood pressure readings.

Piezoelectric crystals are capable of measuring blood pressure by converting blood pressure into an electrical potential, and of being used to derive a blood flow measurement using the measured blood pressure and time. Piezoelectric crystals sense a change in a mechanical-to-electrical transduction. FIGS. 15–17 illustrate blood flow ($\alpha$), blood pressure ($\beta$), and electrical potential (E) for a given blood flow and pressure. FIG. 15 is a graph illustrating blood flow ($\alpha$) as derived from time and sensor readings of pressure. FIG. 16 is a graph illustrating blood pressure ($\beta$) as determined by sensor readings. FIG. 17 is a graph illustrating electrical potential (E) as determined by sensor readings, which corresponds to blood flow and blood pressure readings. It is noted that all of the waveforms are scaled versions of each other. According to various embodiments, piezoelectric crystals are used to indicate restenosis, artery occlusion or first time stenosis, and blood pressure for cardiac output function.

Capacitive membrane sensors, like piezoelectric crystals, are capable of measuring blood pressure by converting blood pressure into an electrical potential, and are capable of being used to derive a blood flow measurement using the measured blood pressure and time. Capacitive membrane sensors operate to sense a change in capacitance. According to one embodiment, a capacitive membrane sensor is used to sense rate. In this rate-sensing embodiment, the required resolution is not as high as is required for sensing blood pressure and/or blood flow. The rate-sensing embodiment provides a mechanical rate indicator of the pulsing blood versus an electrical rate indicator of the local cell depolarization. According to one embodiment, a capacitive membrane sensor is used in conjunction with an electrically-based rate indicator to determine if a pulseless electrical activity (PEA) or electro mechanical disassociation (EMD) has occurred by monitoring the cardiac output via the pressure measurement or by measuring the area under the curve to determine the cardiac output/stroke volume measurement.

Figure 18:
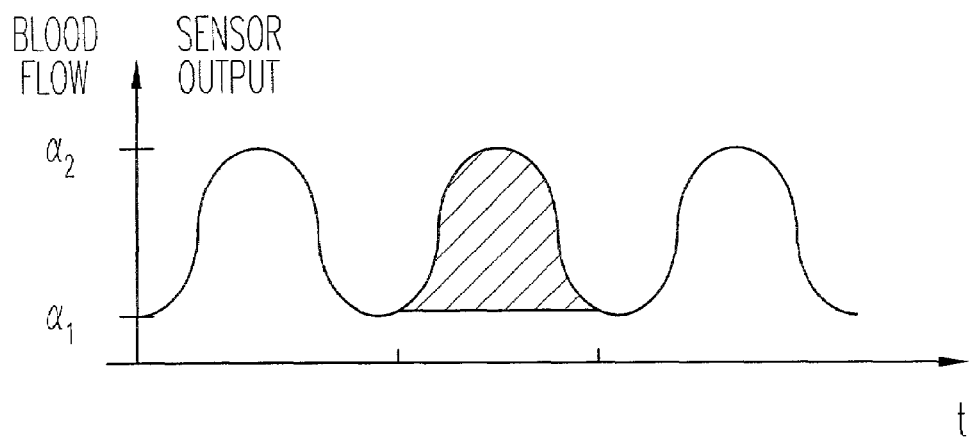
FIG. 18 is a graph illustrating blood flow, as derived from sensor readings of pressure, wherein the area under the curve represents a cardiac output/stroke volume measurement and the width and height of pulses represent contraction speed and peak pressure.
Figure 19:
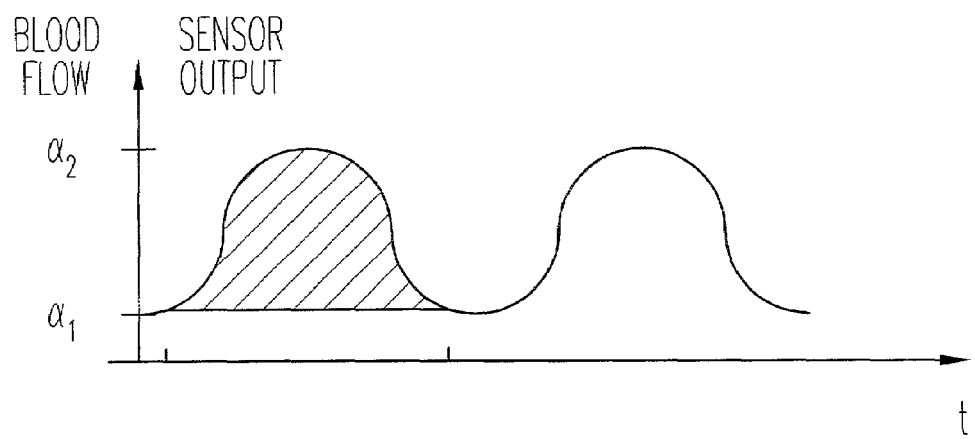
FIG. 19 is another graph illustrating blood flow, as derived from sensor readings of pressure, wherein the area under the curve represents a cardiac output/stroke volume measurement and the width and height of pulses represent contraction speed and peak pressure.

FIG. 18 and FIG. 19 are graphs illustrating blood flow, as derived from sensor readings of pressure, wherein the area under the curve represents a cardiac output/stroke volume measurement and the width and height of pulses represent contraction speed and peak pressure. The area under the curve in FIG. 18 may be the same as the area of the curve in FIG. 19. However, the speed of contraction and the peak pressure can be significantly different.

One embodiment of the chronically-implanted devices uses the capacitive membrane as a hemodynamic sensor. For example, if the overall volume pumped through is the same during ventricular tachycardia (VT) as in a normal sinus rhythm (NSR), and the measured pulses are periodic, then the VT may be considered hemodynamically tolerable.

Oxygen sensors have been included previously in pacing leads. Measuring the amount of oxygen in the blood may be used to determine rate parameters, i.e., rate adaption. Oxygen sensors tend to suffer from coagulation on the detector and/or emitter. According to one embodiment, if suffering from coagulation, the oxygen sensor itself serves as a measure of intra vessel coagulation rate.

Oxygen saturation is the amount of oxygen bound to hemoglobin in the blood. Oxygen saturation is expressed as a percentage of the maximum binding capacity. Optical techniques are the most common methods used to measure oxygen saturation in vivo. One embodiment of the chronically-implanted device includes a sensor for measuring oxygen saturation. According to one embodiment, the chronically-implanted device that includes a sensor for measuring oxygen saturation is positioned to measure oxygen on the venous side of the heart.

Figure 20:
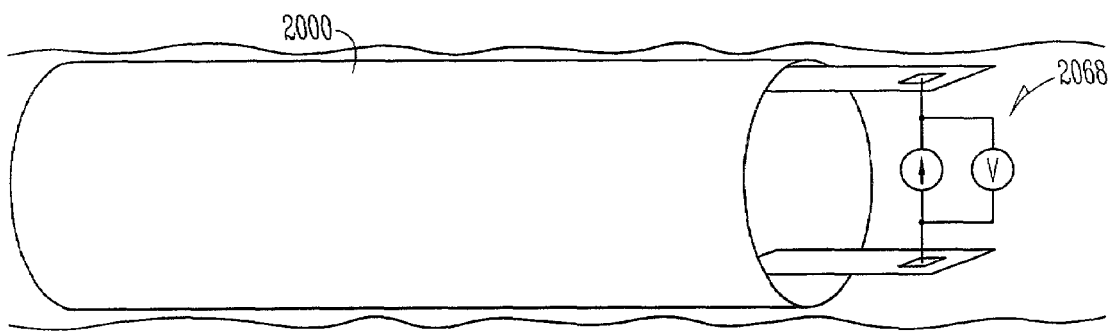
FIG. 20 illustrates one embodiment of an impedance sensor attached to an intravascular stent.

According to one embodiment, an impedance sensor measures the inner diameter of a vessel wall to either monitor the progression or to prevent stenosis or restenosis. FIG. 20 illustrates one embodiment of an impedance sensor 2068 attached to an intravascular stent 2000. A current is injected and the resulting voltage is measured. Impedance is calculated from the known current and voltage. The resistivity ($\rho$) of blood is generally constant for a particular patient, and is provided by resistance per unit length (k$\Omega$/cm). Therefore, a change in impedance reflects a change in the inner wall diameter, as provided by the equation:

$$\Delta R = [\rho blood] \times [\Delta CM].$$

The change in impedance may be caused by local coagulation/fibrosis around the device and/or electrodes over periods of time. One application uses the impedance sensor in conjunction with the piezoelectric crystal and/or capacitive membrane to monitor coagulation/fibrosis build-up. That is, typically the degradation of the impedance signal suggests restenosis since the diameter is decreasing. However, restenosis has not occurred if the blood pressure and/or blood flow as sensed by the piezoelectric crystal and/or capacitive membrane show no degradation. Rather, it is determined that coagulation and/or fibrosis has corrupted impedance-sensing electrodes.

Drug-Eluting Function.

MIT has presented findings related to uncapping a closed planar reservoir to deliver a drug contained within the reservoir. One embodiment of the chronically-invasive device, and in particular the intravascular device, uses such a reservoir to release drugs directly into the vascular system.

One embodiment of the chronically-implanted device carries the drug between a substructure and an electro-erodible overcoat layer; and another embodiment of the chronically-implanted device carries the drug using a drug delivery "chip" that is separately prepared and subsequently attached to the device. The drug is released from the drug delivery chip through an electro-erodible release mechanism. Progressive drug release is provided by wells or regions that are selectively opened by explicitly addressing a given well or region, or by a more generalized progressive erosion of a tapered thickness electro-erodible overcoat layer.

In one embodiment, the erosion process is open-loop where a well understood time-erosion behavior is known. In another embodiment, the erosion process is closed-loop where the erosion progress is monitored using the known relationship among current, voltage and erosion profile. Either process provides control of the eroded capping layer and consequent drug release.

According to one embodiment of the chronically-implanted device, a stent is formed from a malleable, expandable, and substantially cylindrical mesh of biocompatible material. The construction of the stent includes at least one full length or truncated longitudinal region of non-mesh construction. A drug release chip is bonded to a longitudinal region of the stent or a similar longitudinal region of the base stent material that has been suitably prepared as a substrate for further drug-release construction. The stent structure is placed in a vascular region using conventional means known to one of ordinary skill in the art.

One embodiment of the drug release chip includes an array of well-like structures constructed so as to laterally isolate one well from another well so that one well is able to be selectively exposed using an electro-erodible process, for example, to deliver a specific drug type and drug dose. An electrically insulating layer covers the well(s) and the surrounding regions. One or more drugs are contained within the well(s). A cap layer of electro-erodible material covers the well(s). The electro-erodible material is non-toxic to the host biosystem both before and after electro-erosion. One example of an electro-erodible material is gold.

In one embodiment, the connections and cap layer are patterned to allow individual well caps to be selected for electro-erosion using addressing logic. An electrically insulating, passivation covering insulates all interconnections except the intended electro-erosion region over and perhaps immediately around the drug release well. Alternatively, one or more thickness-graded capping layer(s) are selectively and progressively electro-eroded resulting in controlled progressive exposure of wells in the thinner capped region first. In various embodiments, a current, for a voltage-activated electro-erosion process, or a developed potential, for a current-activated electro-erosion process, are monitored to control the electro-erosion process.

The drug-eluting device includes a controlled activation that is powered either by a controlled power source or by a self-contained power system. The controller power source is similar to that used in pacemaker technology, such as a battery contained in a hermetic biocompatible enclosure. The electrical connection between the drug release chip and the power source pierces the containing vessel and is sealed using conventional transvenous sealing technology. The self-contained power system includes an encapsulated electrochemical or other energy source, and environmental energy such as a biofuel.

Figure 21:
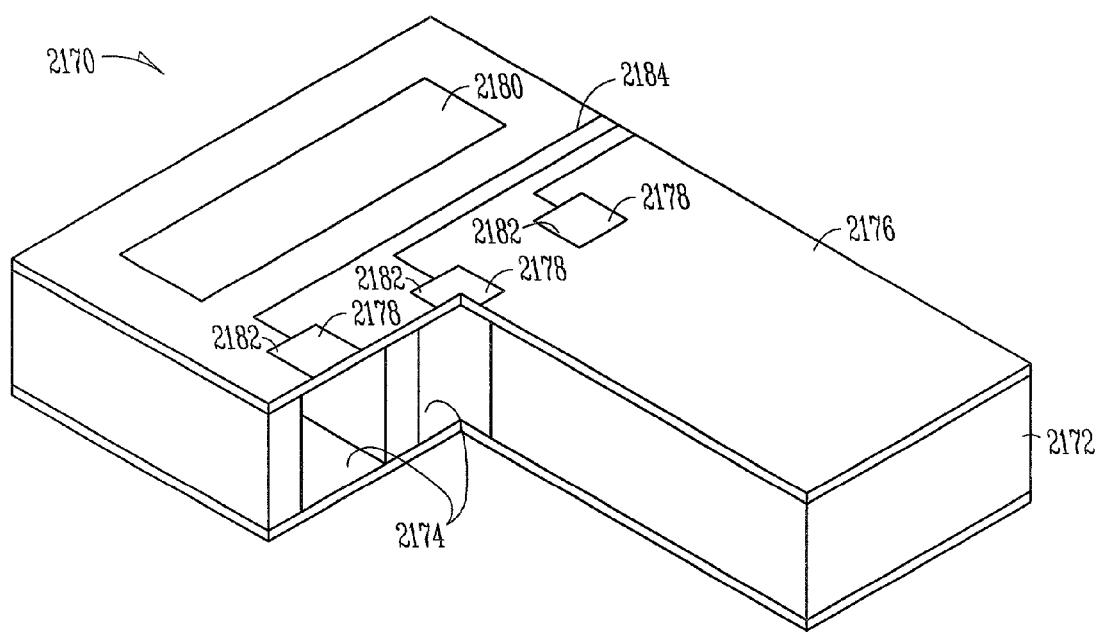
FIG. 21 illustrates one embodiment of a drug delivery microchip for use in one embodiment of a drug-eluting, chronically-implanted device.

FIG. 21 illustrates one embodiment of a drug delivery microchip 2170 for use in one embodiment of a drug-eluting intravascular device. According to this embodiment, a silicon substrate 2172 is formed with voids, wells or micro-reservoirs 2174. These micro-reservoirs 2174 have a sufficient size, are appropriately lined and are otherwise adapted to store an active substance (e.g. drug) to be released into a biosystem. A coating 2176 is formed over the silicon substrate. Electro-erodible caps 2178 are formed in the coating over the wells such that, upon being eroded, an opening is formed between the well and the surrounding biosystem. At least one cathode 2180 and least one anode 2182 are formed in coating 2176. According to one embodiment, the at least one anode forms the electro erodible cap 2178. Wiring 2184 is used to control, or address, the anode to be electro eroded.

Figure 22:
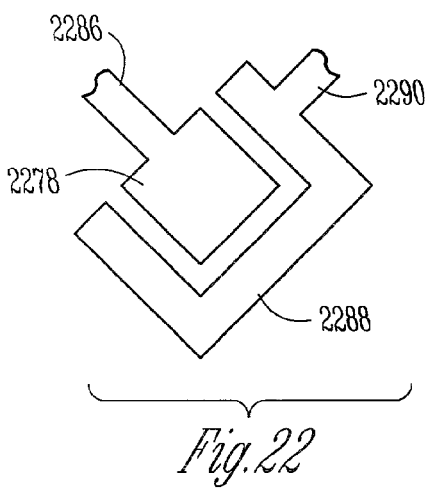
FIG. 22 illustrates one embodiment of a capped, drug-containing well for a drug-eluting, chronically-implanted device.

FIG. 22 illustrates one embodiment of a capped drug-containing well for a drug-eluting, chronically-implanted device. A control line 2286 is connected to a first electrode 2278 that functions as a cap for a well or reservoir. The illustrated embodiment provides a second electrode 2288 that partially surrounds the cap. A second control line 2290 is connected to the second electrode 2288.

Figure 23:
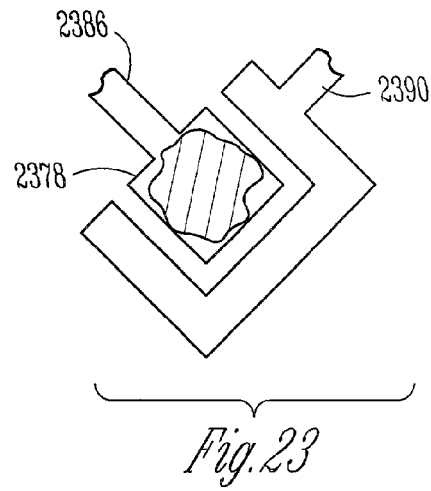
FIG. 23 illustrates an eroded cap for the drug containing well of FIG. 22.

FIG. 23 illustrates an eroded cap for the drug containing well of FIG. 22. The illustrated cap 2378 is electro-eroded using the control lines 2386 and 2390. Once eroded, the active substance, or drug, contained within the reservoir is eluted or dispensed into the biosystem.

Figure 24:
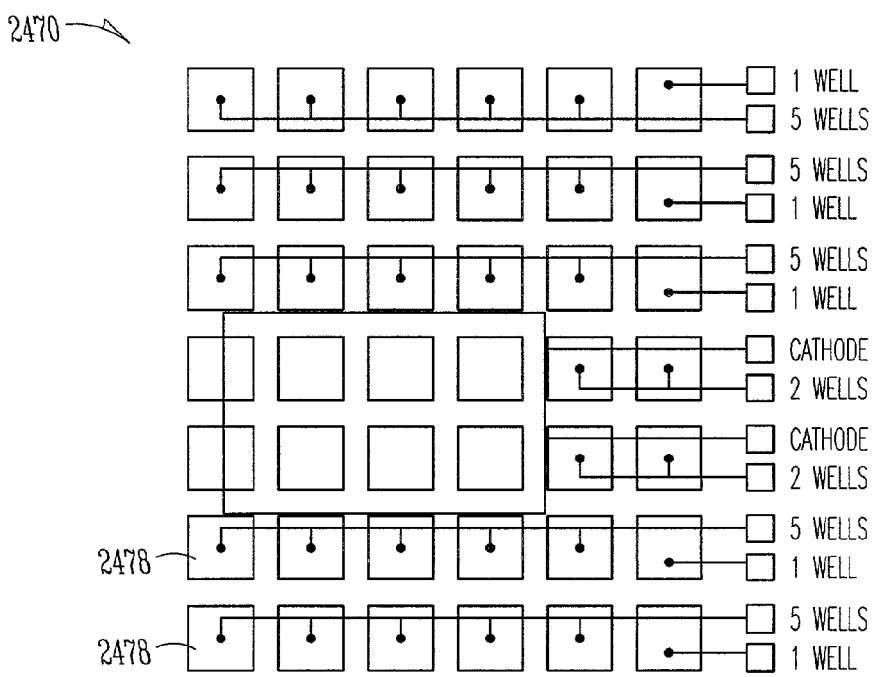
FIG. 24 illustrates one embodiment of a drug delivery microchip capable of delivering different drugs and different dosages of the drugs as part of a drug-eluting chronically-implanted device.

FIG. 24 illustrates one embodiment of a drug delivery microchip 2470 capable of delivering different drugs and different dosages of the drugs. The wells within the microchip are addressable; that is, addressable control lines are used to select the wells or well-combinations whose caps 2478 are to be electro eroded to elute the active substance contained therein. In the illustrated electrode configuration, there are five sets of one well, five sets of five wells and two sets of two wells. The different sized sets provide different delivery dosages. Alternatively, the physical size of the wells themself are used to control the delivery dosage. Additionally, different drug types are able to be stored in the different sets of wells, such that a desired drug among several is able to be dispensed upon the detection of a particular event.

Satellite-Planet Configuration.

Figure 25:
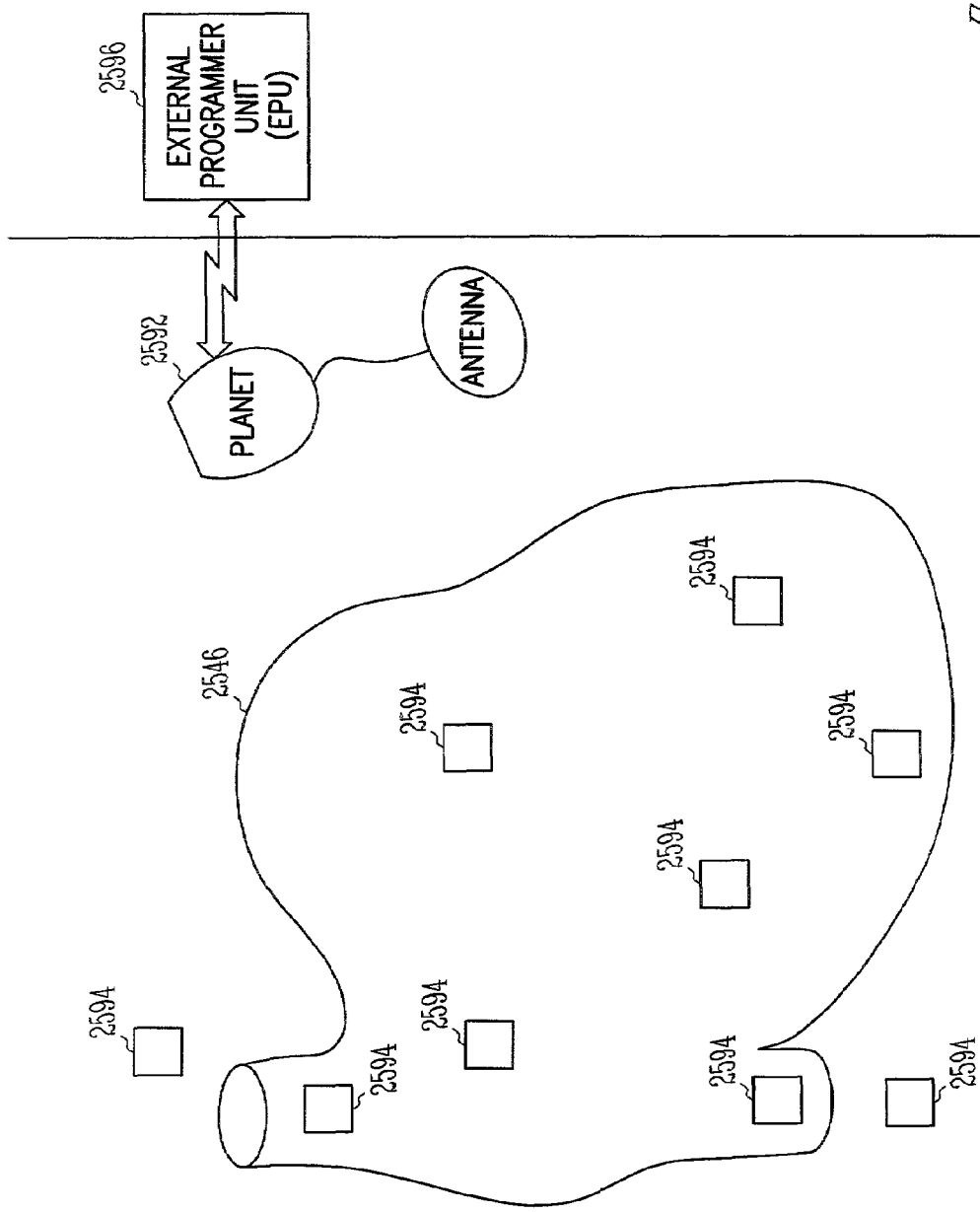
FIG. 25 illustrates an implantable medical device network including a planet and a plurality of satellites, wherein the satellites are formed by the chronically-implanted device of the present subject matter.

According to one embodiment, the chronically-implanted device is incorporated as one or more satellites in a satellite-planet configuration. FIG. 25 illustrates an implantable medical device network including a planet 2592 and a plurality of satellites 2594 formed by the chronically-implanted device. The planet 2592 provides one example of an external device as illustrated and described with respect to FIGS. 1–3. The satellites are shown proximate to a heart 2546. The satellites are capable of being placed throughout a biosystem according the desired application.

In general, the planet is implanted or externally retained. The planet is capable of wirelessly communicating, i.e. without a direct electrical connection, to each satellite, or is capable of being tethered to each satellite. The planet individually commands each satellite to provide sensing functions and therapy functions such as delivering electrical pulses or drugs. In another embodiment, the satellites function autonomously with respect and are in communication with the planet. This communication is initiated by the planet and/or by the satellite in various embodiments. Additionally, each satellite is capable of determining when a sense event has occurred, along with an identifying code indicating to the planet which satellite detected the sense event. In one embodiment, the planet processes the encoded signals received from the network of satellites, assigns time values to each satellite when that satellite detects a sense event, compares the time values to a template of normal time values, and determines if a therapy should be applied. Further, the planet selects and applies the appropriate therapy for the sensed event. According to one embodiment, the satellites derive their needed power from signals received from the planet via the wireless communication path or through a tether. In various embodiments, the satellites are self-powered using a battery or biofuel cells. In one embodiment, the planet is programmable using an external programmer unit 2596.

Figure 26:
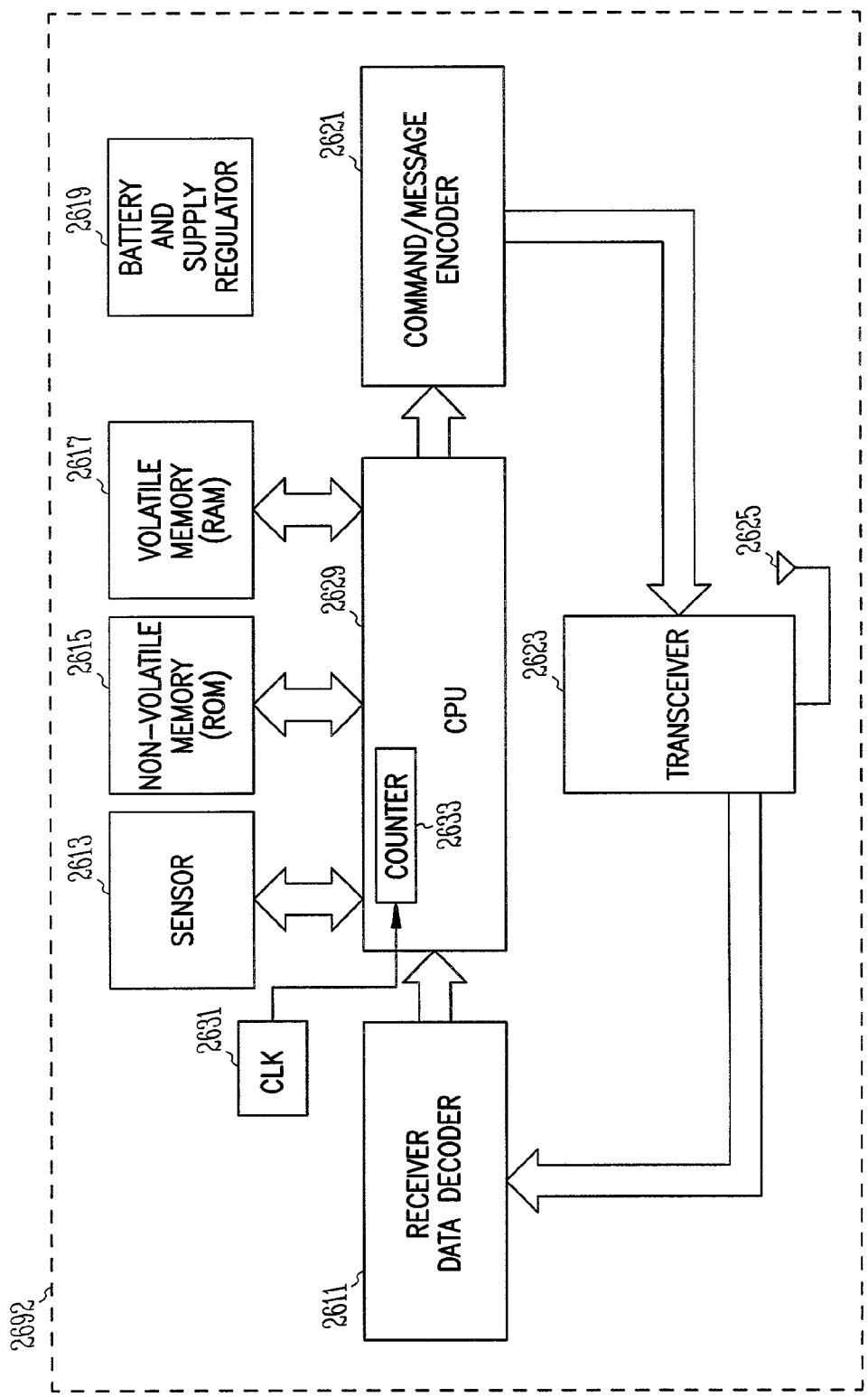
FIG. 26 is a block diagram illustrating the interconnection between the various components and circuitry for one embodiment of the planet of FIG. 25.

FIG. 26 is a block diagram illustrating the interconnection between the various components and circuitry for one embodiment of the planet of FIG. 25. The planet 2692 generally includes a receiver data decoder 2611, a sensor or sensors 2613, a non-volatile memory (e.g. ROM) 2615, a volatile memory (e.g. RAM) 2617, a battery and supply regulator 2619, a command/message encoder 2621, a transceiver 2623, an antenna 2625, and a central processing unit (CPU) 2629. This embodiment of the planet also includes a clock generator 2631 that provides a periodic timing signal to a counter 2633 which may be included as part of the CPU. Other components may be included in planet as desired.

The CPU preferably includes any suitable type of commercially available processor or may be a custom design. The CPU controls the operation of planet. Generally, the CPU processes data received from the satellites via the transceiver and antenna, and receiver data decoder. The CPU also initiates the transmission of commands to each satellite individually by conveying a message to the command/message encoder which, in turn, provides an encoded message to be transmitted through antenna via transceiver. The CPU also receives inputs from the sensor, ROM, RAM, and clock. The non-volatile memory is used to store configuration and program code for execution by the CPU. Volatile memory (RAM) is used as "scratch-pad" memory for storing data used by the CPU.

The battery and supply regulator preferably provides electrical power for the circuitry of the planet. The construction of the battery preferably uses a chemistry known to one skilled in the art. For example, the battery may include a disposable lithium iodide cell, but may employ rechargeable cells as well. The use of a rechargeable battery permits the planet's size to be smaller than if a non-rechargeable battery is used because a rechargeable battery need not hold as much charges as a disposable battery. A rechargeable battery, however, requires periodic recharging by an external device. An exemplary rechargeable battery may employ a lithium-ion chemistry. If a rechargeable battery is used, the planet preferably includes a coil or wire to capture inductively-coupled energy from an external device. As previously described with respect to the chronically-implanted device, other power generators, such as biofuel cells, may be used to power the planet.

In one embodiment, the satellites transmit signals via wireless communication links to the planet. The transmitted signals are detected by the planet's antenna and demodulated in transceiver. The antenna preferably includes a coil of wire, parallel plates, dipoles or other suitable types of antennae to launch or capture electromagnetic energy. According to one embodiment, the satellites are a stent-like intravenous, chronically-implanted devices, and their antenna are formed by the stent-like device. According to other embodiments, the antenna is implemented as other types of transducers, such as ultrasonic (piezoelectric) devices. The transceiver includes modulators, demodulators and splitters for processing the signal from the antenna. The wireless communication technique is selected from any suitable technique.

The output signal from the transceiver also is provided to the receiver data decoder. The demodulation method used by transceiver is appropriate for the communication methodology implemented via the pacer network for transmitting signals between satellites and the planet, such as frequency demodulation, amplitude demodulation or phase shift keying demodulation. The demodulated signal from transceiver is coded by receiver data decoder and provided in digital form to CPU over a digital bus.

The master clock generates a periodic timing signal which is provided to counter. The counter may be included as part of the CPU or may be a discrete device coupled to the CPU.

The counter counts cycles of the periodic timing signal generated by clock. The CPU can read the counter to determine the current count value. For example, if the clock signal is 1000 Hz and a counter counts 500 cycles of the clock signal, the CPU will know that the counter has counted for one-half of a second. In one embodiment, the counter preferably is implemented as a "count up" counter and a provides an output count value that begins with 0 and increments by 1 for each cycle of the periodic timing signal. Preferably the CPU is able to reset the counter to begin counting again from 0.

In operation, each satellite in one embodiment transmits a signal to the planet when the satellite detects a sense event. According to various other embodiments, each satellite is adapted to autonomously sense continuously, periodically, or other method, and/or to sense on demand by the planet. The CPU uses the count value read from counter to determine when the sense event (reported by a satellite) has occurred during each cardiac cycle. Upon receiving a sense event signal from a satellite, the planet reads the current count elapsed since the counter was last reset. The CPU may have been programmed to reset the counter at or near the beginning of each cardiac cycle and thus, the count value read by the CPU is indicative of when the sense event occurred during the cardiac cycle. Alternatively, the count value may be latched in a register (not shown) while the counter continues.

Figure 27:
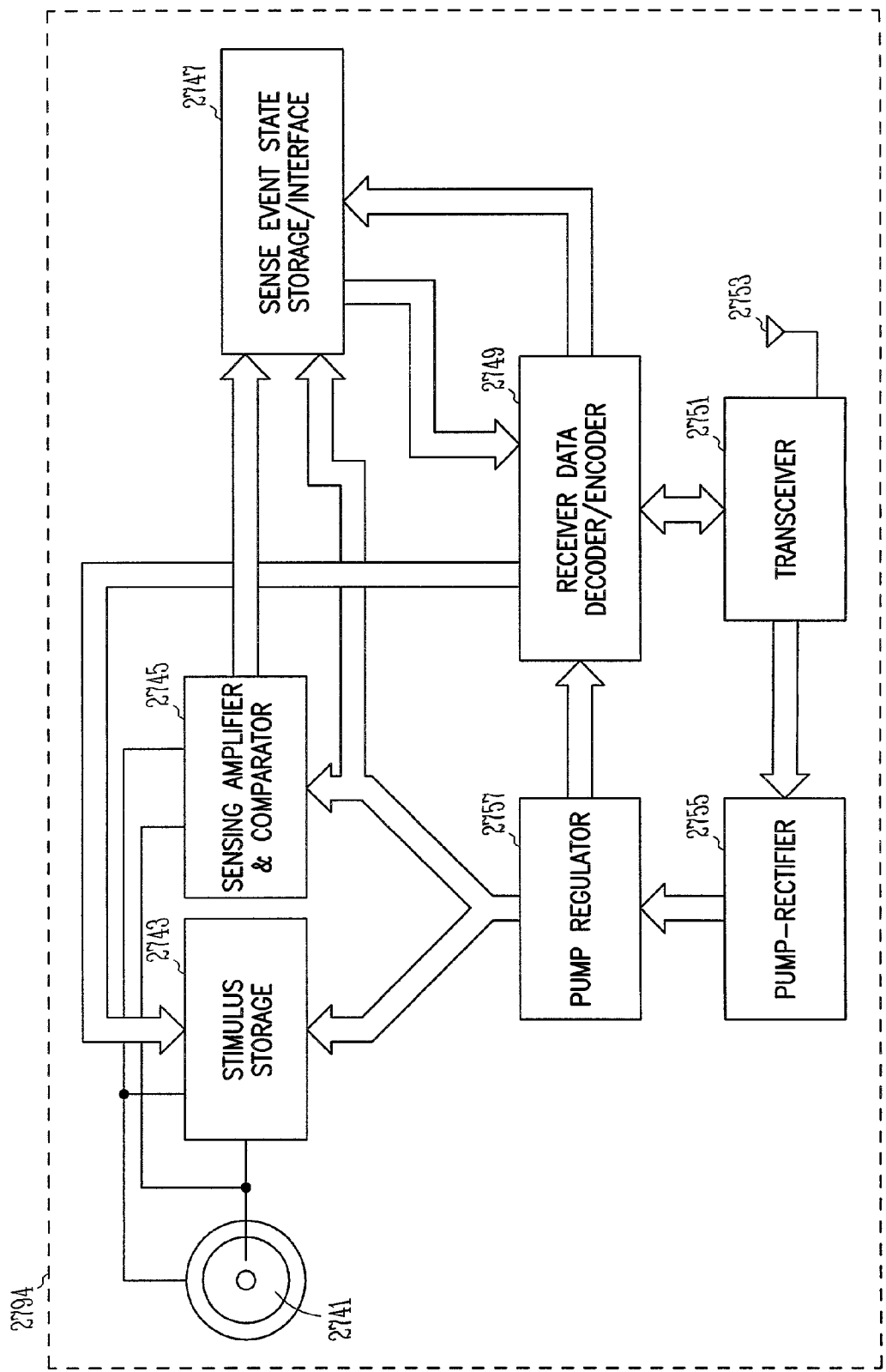
FIG. 27 is a block diagram illustrating the interconnection between the various components and circuitry for one embodiment of a satellite of FIG. 25.

FIG. 27 is a block diagram illustrating the interconnection between the various components and circuitry for one embodiment of a satellite of FIG. 25. More than one satellite 2794 may be used in the satellite-planet configuration and each satellite is constructed the same or similar to the satellite depicted in FIG. 27. One satellite embodiment includes a pair of electrodes 2741, a stimulus storage unit 2743, a sensing amplifier and comparator logic 2745, a sense event state storage and interface 2747, a receiver data decoder/encoder 2749, a transceiver 2751, an antenna 2753, a pump-rectifier 2755, and a pump-regulator 2757. According to various embodiments, the satellite is designed for mechanical, electrical and/or chemical sensing, and for mechanical, electrical and/or drug-eluting therapies.

As described in more detail above, the electrical power for the satellite circuitry is provided by battery, by the biofuel cell, and/or by a wired or wireless connection to the planet or some other external device. In one embodiment, the electrical power is derived from the electromagnetic energy received from the planet. One embodiment uses some of the electromagnetic energy to recharge a battery in each satellite. In the illustrated embodiment, the transceiver and antenna receive electromagnetic energy from the planet on which encoded data is superimposed. The received energy is rectified by the pump-rectifier and regulated by the pump-regulator. The pump regulator uses the signal received from the antenna to supply a constant voltage to the other circuits of the satellite when the energy stored in the pump regulator has reached a threshold value. Alternatively, the pump-regulator may comprise a constant voltage reference device in order to stabilize sensing and stimulus storage.

The pump-rectifier and pump regulator process the electromagnetic signal normally received by the antenna. Thus, the signal received from the planet serves to transfer commands and configuration data and to transfer energy for powering the satellites's electronics. Accordingly, even if the planet does not need to communicate commands or configuration data to a satellite, it maybe desirable for the planet to transmit a signal to the satellite simply to keep the satellites' electronics active. Thus, according to one embodiment, the planet briefly communicates with each satellite in the network one at a time to ensure that all satellites are active.

Illustrative Applications.

The description that follows provides illustrative applications which use various aspects of the chronically-implanted device, including one or more of the following: mechanical sensing, electrical sensing, chemical sensing, mechanical therapy, electrical therapy, and drug-eluting/chemical therapy. These illustrative applications are provided as examples, and are not intended as an exclusive list of applications. One of ordinary skill in the art will understand, upon reading and comprehending this disclosure, how to incorporate the various functions of the device of the present subject matter to perform other desirable applications.

One application involves sensing blood pressure, blood flow, and vessel diameter. In one embodiment, the chronically-implanted device is used in a system for detecting ischemia episodes, including silent ischemia. Silent ischemia is a condition in which the tissue become ischemic, but without any associated pain. The ischemia episodes are able to be detected acutely using these applications. In various embodiments, the chronically-implanted device is used in a system for monitoring stenosis and/or restenosis, for detecting cardiac function, for discriminating hemodynamically stable blood pressure and compromised blood pressure associated with a ventricular tachycardia (VT) or bradycardia event, and for detecting electro mechanical dissociation (EMD). EMD is a situation in which, for example, the electrical activity of the heart appears normal but in which the heart is not effectively pumping blood. In one embodiment, the chronically-implanted device is used in a system to measure reduced blood flow and vessel diameter to indicate an acute ischemic episode. Ischemia detection is useful for predicting and is a promising strategy for preventing ventricular arrhythmia and sudden cardiac death. According to one embodiment, the chronically-implanted device continuously tests for silent ischemia, a condition in which patients suffer ischemia with no pain. The intravascular measurement of reduced blood flow is measured directly rather than the indirect, traditional electrical measurements.

According to one aspect of the present invention, the chronically-implanted devices are used as vessel stents that function as arterial-based ischemic detectors for sensing closure of the vessels. CAD is prevalent among ICD patients, and may lead to ischemic episodes that precipitate VT/VF. One promising strategy for predicting certain VT/VF events and applying preventive therapy includes sensing these ischemic episodes. Stents are placed in vessels that have already exhibited levels of occlusion and are likely to exhibit future occlusion. According to one embodiment, detecting these changes provides a warning of ischemic onset independently or in conjunction with electrogram morphology. According to one embodiment, the resonance of the metal stents following an acoustic input depends on the surrounding blockage and/or blood flow.

In one embodiment, the chronically-implanted device is used in a system to chronically measure reduced vessel diameter or blood flow to indicate a gradual restenosis of a vessel. This embodiment is a promising strategy for providing a beneficial warning and permitting a preventive, vascular intervention. This continuous monitoring for restenosis by the chronically-implanted device provides a beneficial warning for initiating preventive, vascular intervention, and reducing the number of patient follow-ups and/or angiograms through the continuous monitoring of restenosis.

In one embodiment, the chronically-implanted device is used in a system for detecting reduced blood pressure to indicate compromised cardiac function in terms of contractility or ejection fraction and stroke volume. In one application, intravascular monitoring for reduced blood pressure is used to monitor heart failure patients and/or efficacy of heart failure therapy.

In one embodiment, the chronically-implanted device is used in a system for detecting reduced blood pressure and/or reduced blood flow and for detecting electrically-determined rate information to discriminate between hemodynamically stable ventricular tachycardia (VT) and VT in which the blood pressure is compromised. Hemodynamically stable VT is an event in which a stimulation pulse may not be required, whereas VT in which the blood pressure is compromised is an event in which a stimulation shock is required. This discrimination capability reduces the number of inappropriate shocks. Additionally, in one embodiment, the intravascular device is used in a system for collecting multiple intravascular measurements to discriminate between regional ischemia and global ischemia, which provides an indication of a hemodynamically compromised VT.

According to one sensor application, the flow and/or pressure within the vessel is measured, and a prophylactic device is inserted within the vessel at a strategic point to monitor several of its "downstream" vessels. For example, by placing such a device in the left interior descending artery, it is possible to detect occlusions in the artery as well as its branches.

In one embodiment, the chronically-implanted device is used in a system for measuring intravascular pressure and for measuring electrical rates to indicate electromechanical dissociation or pulseless electrical stimulation/activation. Occasionally, following shocks to treat VF, little or no mechanical activity occurs, yet the intrinsic or paced electrical activity appears normal. Devices that rely on electrical sensors have difficulty recognizing this condition.

One application involves providing electrical stimulus pulses. In one embodiment, the chronically-implanted device is used in a system for improving hemodynamics. For example, the system is used in heart failure patients to monitor hemodynamic parameters and to improve blood circulation or provide prevention therapies.

According to one embodiment, the chronically-implanted device, or more particularly an intravascular device, is used in pacing applications. One advantage is that the implantation procedure is less invasive for a chronically-implanted device rather than other epicardial electrodes. Another advantage of intravascular pacing includes the increase in available numbers of pacing sites. Another advantage of intravascular pacing includes the increase in available locations for pacing sites. Multisite pacing is considered a promising strategy for improving arrhythmic management and prevention. Two particular embodiments are discussed below.

According to one embodiment, multisite pacing is used as a strategy for improving hemodynamics. Bi-atrial pacing and, more recently, bi-ventricular pacing have been shown to improve cardiac function, especially in heart failure patients. A system according to the present invention, in which several electrodes are placed in one chamber and/or multiple chambers, is a strategy for improving the synchronization and cardiac output in a variety of disease settings.

According to one embodiment, multisite pacing is used as a strategy for managing arrhythmia and/or preventing arrhythmia. For example, antitachycardia pacing (ATP) relies on pacing during the excitable gap to electrically capture or control a heart in sustained VT. It is noted here that one embodiment of the invention provides the ability to sense to determine the location of the excitable gap. The incorporation of more pacing sites provides greater control and more sophisticated ATP strategies. Furthermore, the ability to pace-capture a site during VF has been demonstrated. According to one embodiment, multisite pacing is used as a strategy to pace-capture the heart and/or chamber out of VF rather than to deliver a shock to bring the heart out of VF. According to other embodiments, multisite pacing, sub-threshold stimulation, or a combination thereof is used as a strategy for suppressing local arrhythmia or interrupting a developing re-entrant arrhythmia.

One application involves sensing blood sugar levels, and maintaining the appropriate blood sugar levels by eluting an appropriate substance or substances to controllably raise or lower the blood sugar levels, as required.

According to one embodiment, the chronically-implanted device functions as satellite and communicates to a planet. In a multisite embodiment, multiple intravascular devices are placed as satellites around and are in communication with the planet. According to one embodiment, the satellite intravascular devices are tethered to the planet using a thin connector running from each satellite device through the vessel and to the planet. In this embodiment, each satellite intravascular device functions as a tip, with all of the capabilities of a normal pacing lead tip. According to other embodiments, the satellite lead devices communicate with the planet using wireless techniques such as RF communication or ultrasonic communication or wired techniques.

The chronically-implanted device is capable of providing sensing functions and therapy functions. According to one embodiment, the intravascular device possesses only sensing capabilities. According to this embodiment, there may be either one-way communication or two-way communication between the intravascular device and a central unit, such as between satellites and the control unit. In various sensing-only with one-way communication embodiments, the period is based on battery life and/or a measured parameter such as the average time to restenosis. In various sensing-only with two-way communication embodiments, the periodic sensing is triggered by the planet to sense and/or sense data and/or status.

According to one embodiment, the chronically-implanted device possesses stimulating capabilities without sensing capabilities. According to this embodiment, there may be either one-way communication or two-way communication between the chronically-implanted device and a central unit, such as between satellites and the control unit. In various stimulating-only with one-way communication embodiments, the period is based on battery life and/or a measured parameter such as the average time to restenosis. In various stimulating-only with two-way communication embodiments, the periodic stimulation is triggered by the planet.

According to one embodiment, the chronically-implanted device possesses both sensing and stimulating capabilities as described above. According to one embodiment, multiple, stent-like intravascular devices serve as satellite devices to a planet device.

According to one embodiment, the chronically-implanted device is used as a remote sensing mode. In one embodiment, a pacemaker or implantable defibrillator with increased sense amplifier bandwidth detects the higher frequency electric fields generated by a stent based system and separates them by frequency filtering from other physiologic signals. One embodiment of the stent system includes a radially split stent acting as a dipole electric field antenna, and a pressure sensor integrated into a communication microsystem that is placed in a vein or artery. The microsystem power source provides energy for the sensor, communication and computation circuits. For example, the sensor measures peak pressure upon each cardiac cycle, and is capable of electively transmitting the latest measurement as a small packet of data that contains variation data from the last transmitted value. The data packet is able to be transmitted using various schemes. A self-clocking scheme for data encoding is particularly simple and reliable to decode.

According to one embodiment, the chronically-implanted device functions as a repeater for remote sensors that provides two-way linking of distributed system nodes. The repeater listens for transmissions of data and data acknowledgments. The repeater matches traffic packets and, if an acknowledgment did not occur within a predefined time period, the repeater echoes the received data packet. The repeater function need not be a stand-alone function, as it can be combined with other functions on the chronically-implanted device. In one embodiment, intermediate computation is added to reduce, combine or evaluate data streams.

According to one embodiment, the chronically-implanted device provides a therapy based on local and/or remote data. According to various embodiments, the therapy includes drug-eluting therapy and electrical therapy.

According to one embodiment, the intravascular device provides stroke/heart attack first aid by infusion of aspirin or other drug. It is recognized that an increasing number of drugs are able to treat the debilitating affects of a stroke or a heart attack if a victim can receive a dose shortly after the event. An electrically controlled drug-eluting stent, when combined with suitable stroke or heart attack sensing technology, provides one or more controlled releases of a first-aid drug. One example of a first aid drug includes a blood-thinning agent such as aspirin and the like. In various embodiments, the amount of drug dispensed is controlled by clinician presets and automatic presets, if adequate sensing is available, to compensate for factors such as body weight or proximity of the stent to the traumatized area.

The figures presented and described in detail above are similarly useful in describing the method aspects of the present subject matter. The methods described below are nonexclusive as other methods may be understood from the specification and the figures described above.

One aspect provides a method in which a device is inserted intravascularly into a biosystem. The device is used to sense a mechanical parameter and to provide therapy. In one embodiment, a stent is inserted intravascularly into the biosystem. In one embodiment, the device is arterially inserted. In one method embodiment, a plurality of devices are inserted intravascularly into a biosystem to function together as a system.

According to various embodiments of the method, the mechanical parameters sensed using the device include blood pressure, blood flow, and/or vessel size. According to various methods, the method further includes sensing oxygen, ions, coagulation, fibrosis, catecholamines, and/or intrinsic electrical signals generated by excitable tissue.

According to various embodiments of the method, the therapy provided by the device includes stimulating electrically excitable tissue such as providing cardiac stimulus signals, eluting drugs to improve biocompatibility, eluting drugs in response to a detected stroke condition, eluting drugs in response to a detected heart attack condition and/or eluting an active substance in response to a sensed blood sugar level.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:

1. A device, comprising:
  a stent-like structure adapted to be chronically placed within a vessel of a biosystem;
  sensing circuitry attached to the structure and adapted to be placed in the vessel with the structure, wherein the sensing circuitry is adapted to sense mechanical parameters in the biosystem; and
  therapy-providing circuitry attached to the structure and adapted to be placed in the vessel with the structure, wherein the therapy-providing circuitry is adapted to provide electrical therapy to the biosystem.

2. The device of claim 1, wherein the stent-like structure is adapted to be chronically placed intravascularly in the biosystem.

3. The device of claim 1, wherein the sensing circuitry includes:
  a sensor;
  a sensor reader coupled to the sensor to provide an interface to the sensor;
  a data digitizer coupled to the sensor reader to convert sensor data for transmission over a digital medium; and
  a data encoder coupled to the digitizer to encode the sensor data.

4. The device of claim 3, wherein the sensor includes a pressure-based sensor.

5. The device of claim 4, wherein the sensor includes a piezoelectric crystal.

6. The device of claim 4, wherein the sensor includes a capacitive membrane sensor.

7. The device of claim 3, wherein the sensor includes an oxygen sensor.

8. The device of claim 3, wherein the sensor includes an impedance sensor.

9. The device of claim 3, wherein the sensing circuitry is fabricated using Micro-Electro-Mechanical Systems (MEMS) technology.

10. The device of claim 3, wherein the sensing circuitry is further adapted to sense electrical parameters in the biosystem.

11. The device of claim 3, wherein the sensing circuitry is further adapted to sense chemical parameters in the biosystem.

12. The device of claim 3, wherein the stent-like structure is adapted to be chronically placed intravascularly in the biosystem.

13. The device of claim 1, wherein the therapy-providing circuitry includes:
an output capacitor charging circuit;
a set parameters circuit for adjusting stimulation parameters;
an electrical application circuit operably connected to the output capacitor charging circuit and the set stimulation parameters circuit to provide an electrical signal; and
at least one electrode operably connected to the electrical application circuit and adapted to provide electrical therapy.

14. The device of claim 13, wherein the set stimulation parameters circuit is adapted to adjust pulse width, amplitude stimulation modes, and stimulation site.

15. The device of claim 13, wherein the electrical application circuit includes an inject current circuit.

16. The device of claim 13, wherein the electrical application circuit includes a set voltage circuit.

17. The device of claim 13 wherein the therapy-providing circuitry is adapted to provide pacing therapy to a heart.

18. The device of claim 13, wherein the therapy-providing circuitry is adapted to provide defibrillation therapy to a heart.

19. The device of claim 13, wherein the stent-like structure is adapted to be chronically placed intravascularly in the biosystem.

20. A device, comprising:
a structure adapted to be chronically placed within a vessel of a biosystem:
sensing circuitry attached to the structure and adapted to be placed in the vessel with the structure, wherein the sensing circuitry is adapted to sense mechanical parameters in the biosystem; and
therapy-providing circuitry attached to the structure and adapted to be placed in the vessel with the structure, wherein the therapy-providing circuitry is adapted to provide electrical therapy to the biosystem, said therapy-providing circuitry having drug-eluting circuitry, including:
an active substance;
an electro-erodible covering enclosing the active substance; and
electrodes adapted to controllably erode the electrode covering to controllably release the active substrate.

21. The device of claim 20, wherein the electrodes are addressable to control the drug eluting process.

22. The device of claim 20, wherein the electro-erodible covering is tapered to control the drug-eluting process.

23. The device of claim 20, wherein the therapy-providing circuitry is adapted to provide drug-eluting therapy in response to a heart-attack.

24. The device of claim 20, wherein the therapy-providing circuitry is adapted to provide drug-eluting therapy in response to a stroke.

25. The device of claim 20, wherein the therapy-providing circuitry is adapted to provide appropriate therapy in response to a sensed blood sugar level that is out of a desired range.

26. The device of claim 20, wherein the structure includes a stent-like structure adapted to be chronically placed in the biosystem.

27. The device of claim 26, wherein the stent-like structure is adapted to be chronically placed intravascularly in the biosystem.

28. The device of claim 1, further comprising power circuitry attached to the structure and coupled to the therapy-providing circuitry, wherein the power circuitry is adapted to provide power to the device.

29. The device of claim 28, wherein the power circuitry is adapted to provide power from a battery.

30. The device of claim 28, wherein the power circuitry is adapted to provide power from a biofuel cell.

31. The device of claim 28, wherein the power circuitry is adapted to provide power received wirelessly from an external device.

32. The device of claim 31, wherein the power circuitry is adapted to provide power received by radio-frequency (RE) energy from the external device.

33. The device of claim 31, wherein the power circuitry is adapted to provide power received by ultrasound energy from the external device.

34. The device of claim 28, wherein the power circuitry is adapted to provide power received through a tether that connects an external device to the power circuitry.

35. The device of claim 1, further comprising communication circuitry adapted to communicate with a control unit.

36. The device of claim 35, wherein the communication circuitry includes radio frequency (RF) circuitry for communicating with the control unit using RF waves.

37. The device of claim 36, wherein the RF circuitry includes an RF receiver adapted to receive RF transmission from the control unit.

38. The device of claim 37, wherein the RF circuitry further includes a data extract or coupled to the RF receiver to decode communication in the RF transmission.

39. The device of claim 36, wherein the RF circuitry includes an RF transmitter adapted to transmit RF transmission to the control unit.

40. The device of claim 39, wherein the RF circuitry further Includes a data mixer coupled to the RF transmitter and adapted to encode communication for RF transmission.

41. The device of claim 1, wherein:
the sensing circuitry includes;
a sensor;
a sensor reader coupled to the sensor to provide an interface to the sensor;
a date digitizer coupled to the sensor reader to convert sensor data for transmission over a digital medium; and
a data encoder coupled to the digitizer to encode the sensor data; and
the therapy-providing circuitry includes;
an output capacitor charging circuit;
a set parameters circuit for adjusting stimulation parameters;
an electrical application circuit operably connected to the output capacitor charging circuit and the set stimulation parameters circuit to provide an electrical signal; and
at least one electrode operably connected to the electrical application circuit and adapted to provide electrical therapy.

42. The device of claim 41, wherein:
the sensing circuitry is further adapted to sense electrical parameters within the biosystem; and
the therapy-providing circuitry is adapted to provide electrical therapy to the biosystem.

43. The device of claim 41, wherein: the sensing circuitry is further adapted to sense chemical parameters within the biosystem; and the therapy-providing circuitry is adapted to provide electrical therapy to the biosystem.

44. The device of claim 41, wherein the stent-like structure is adapted to be chronically placed intravascularly in the biosystem.

45. A device comprising:
a structure adapted to be chronically placed within a vessel of a biosystem;
sensing circuitry attached to the structure and adapted to be placed in the vessel with the structure, wherein the sensing circuitry is adapted to sense mechanical parameters in the biosystem, said sensing circuitry including;
a sensor;
a sensor reader coupled to the sensor to provide an interface to the sensor;
a data digitizer coupled to the sensor reader to convert sensor data for transmission over a digital medium; and
a data encoder coupled to the digitizer to encode the sensor data; and therapy-providing circuitry includes;
an active substance;
an electro-erodible covering enclosing the active substance; and
electrodes adapted to controllably erode the electrode covering to controllably release the active; and
therapy-providing circuitry attached to the structure and adapted to be placed in the vessel with the structure, wherein the therapy-providing circuitry is adapted to provide electrical therapy to the biosystem.

46. The device of claim 45, wherein:
the sensing circuitry is further adapted to sense electrical parameters within the biosystem; and
the therapy-providing circuitry is adapted to provide drug-eluting therapy to the biosystem.

47. The device of claim 45, wherein: the sensing circuitry is further adapted to sense chemical parameters within the biosystem; and
the therapy-providing circuitry is adapted to provide drug-eluting therapy to the biosystem.

48. The device of claim 45, wherein the structure includes a stent-like structure adapted to be chronically placed in the biosystem.

49. The device of claim 48, wherein the stent-like structure is adapted to be chronically placed intravascularly in the biosystem.

50. A device, comprising:
a stent-like structure adapted to be chronically placed within a vessel of a biosystem;
sensing circuitry attached to the ant-like structure and adapted to be placed within the vessel with the structure and to sense mechanical parameters within the biosystem;
therapy-providing circuitry attached to the structure and adapted to be placed within the vessel with the structure and to provide electrical therapy to the biosystem; and
control circuitry ached to the ant-like device coupled to the sensing circuitry and the therapy-providing circuitry, wherein the control circuitry is adapted to control sensing operations and therapy-providing operations.

51. The device of claim 50, wherein the ant-like structure is adapted to be chronically placed Intravascularly within the biosystem.

52. The device of claim 51, wherein the stent-like structure is adapted to be placed using a catheter in a relatively noninvasive procedure.

53. The device of claim 51, wherein the stent-like structure is adapted to be placed using a hypodermic needle in a relatively noninvasive procedure.

54. The device of claim 50, wherein the sensing circuitry includes:
a sensor;
a sensor reader coupled to the sensor to provide an interface to the sensor;
a data digitizer coupled to the sensor reader to convert sensor data for transmission over a digital medium; and
a data encoder coupled to the digitizer to encode the sensor data.

55. The device of claim 50, wherein the sensing circuitry includes a pressure-based sensor.

56. The device of claim 55, wherein the sensing circuitry includes a piezoelectric crystal.

57. The device of claim 55, wherein the sensing circuitry includes a capacitive membrane sensor.

58. The device of claim 50, wherein the sensing circuitry includes an oxygen sensor.

59. The device of claim 50, wherein the sensing circuitry includes an impedance sensor.

60. The device of claim 50, wherein the sensing circuitry is adapted to sense hemodynamic parameters.

61. The device of claim 50, wherein the sensing circuitry is adapted to sense blood flow.

62. The device of claim 50, wherein the sensing circuitry is further adapted to sense electrical parameters within the biosystem.

63. The device of claim 62, wherein the sensing circuitry is adapted to detect cardiac arrhythmias.

64. The device of claim 50, wherein the sensing circuitry is further adapted to sense chemical parameters within the biosystem.

65. The device of claim 64, wherein the sensing circuitry is adapted to sense oxygen saturation in blood.

66. The device of claim 64, wherein the sensing circuitry is adapted to sense blood sugar levels.

67. The device of claim 50, wherein the sensing circuitry is fabricated with Micro-Electro-Mechanical Systems (MEMS) technology.

68. The device of claim 50, wherein the therapy-providing circuitry includes:
an output capacitor charging circuit;
a set parameters circuit for adjusting stimulation parameters;
an electrical application circuit operably connected to the output capacitor charging circuit and the set stimulation parameters circuit to provide an electrical signal; and
at least one electrode operably connected to the electrical application circuit and adapted to provide electrical therapy.

69. The device of claim 68, wherein the set stimulation parameters circuit is adapted to adjust pulse width, amplitude stimulation modes, and stimulation site.

70. The device of claim 68, wherein the electrical application circuit includes an inject current circuit.

71. The device of claim 68, wherein the electrical application circuit includes a set voltage circuit.

72. The device of claim 50, wherein the therapy-providing circuitry includes drug-eluting circuitry, including:
an active substance;
an electro-erodible covering enclosing the active substance; and
electrodes adapted to controllably erode the electrode covering to controllably release the active substrate.

73. The device of claim 72, wherein the electrodes are addressable to control the drug-eluting process.

74. The device of claim 72, wherein the electro-erodible covering is tapered to control the drug-eluting process.

75. The device of claim 50, wherein:
the sensing circuitry is further adapted to sense electrical parameters within the biosystem; and
the therapy-providing circuitry is adapted to provide electrical therapy to the biosystem.

76. The device of claim 50, wherein:
the sensing circuitry is further adapted to sense chemical parameters within the biosystem; and
the therapy-providing circuitry is adapted to provide electrical therapy to the biosystem.

77. The device of claim 50, wherein:
the sensing circuitry is further adapted to sense electrical parameters within the biosystem; and
the therapy-providing circuitry is adapted to provide drug-elating therapy to the biosystem.

78. The device of claim 50, wherein:
time sensing circuitry is further adapted to sense chemical parameters within the biosystem; and
the therapy-providing circuitry is adapted to provide drug-eluting therapy to the biosystem.

79. The device of claim 50, further comprising power circuitry attached to the structure and coupled to the sensing circuitry and the therapy-providing circuitry.

80. The device of claim 79, wherein the power circuitry is adapted to provide power from a battery.

81. The device of claim 79, wherein the power circuitry is adapted to provide power from a biofuel cell.

82. The device of claim 79, wherein the power circuitry is adapted to provide power received wirelessly from an external device.

83. The device of claim 79, wherein the power circuitry is adapted to provide power received by radio-frequency (RF) energy from the external device.

84. The device of claim 79, wherein the power circuitry is adapted to provide power received by ultrasound energy from the external device.

85. The device of claim 79, wherein the power circuitry is adapted to provide power received through a tether that connects power from an external device to the power circuitry.

86. The device of claim 50, further comprising communication circuitry adapted to communicate wirelessly to an external device.

87. The device of claim 86, further comprising communication circuitry adapted to communicate to an external device using radio frequency (RE) energy.

88. The device of claim 50, further comprising communication circuitry adapted to communicate to an external device through a tether that connects the device to the external device.

89. The device of claim 50, further comprising communication/power circuitry attached to the structure, wherein:
the communication/power circuitry is adapted to communicate with an external device; and
the communication/power circuitry is adapted to receive power from the external device and power the therapy-providing circuitry, the sensing circuitry, and the controller.

90. The device of claim 89, wherein:
the communication/power circuitry is adapted to communicate wirelessly to the external device using a communication signal; and
the communication/power circuitry is adapted to receive power wirelessly from the external device using a power signal.

91. The device of claim 89, wherein the communication signal is modulated with the power signal.

92. A system, comprising:
a planet; and
at least one satellite device adapted to communicate with the planet, wherein the satellite device includes;
a stent-like structure adapted to be chronically placed within a vessel of a biosystem;
sensing circuitry attached to the structure and adapted to be placed in the vessel with the structure, wherein the sensing circuitry is adapted to sense mechanical parameters in the biosystem; and
therapy-providing circuitry attached to the structure and adapted to be placed in the vessel with the structure, wherein the therapy-providing circuitry is adapted to provide electrical therapy to the biosystem.

93. The system of claim 92, wherein a tether couples the at least one satellite device to the planet.

94. The system of claim 93, wherein the tether provides a data communication channel.

95. The system of claim 93, wherein the tether provides a power connection between the satellite device and the planet.

96. The system of claim 93, wherein the tether includes dedicated data and power lines.

97. The system of claim 92, wherein the satellite device communicates with the planet wirelessly.

98. The system of claim 97, wherein the satellite device communicates with the planet using radio frequency (RF) waves.

99. The system of claim 98, wherein the device structure functions as an antenna for RE communications.

100. The system of claim 92, wherein the satellite device is powered by a battery.

101. The system of claim 92, wherein the satellite device is powered by a biofuel cell.

102. The system of claim 92, wherein the satellite device is powered by radio frequency (RE) energy from the planet.

103. The system of claim 92, wherein the satellite device is powered by ultrasound energy from the planet.

104. The system of claim 92, wherein at least one of the satellite devices functions as a repeater for communication transmissions.

105. The system of claim 92, wherein the sensing circuitry includes:
a sensor;
a sensor reader coupled to the sensor to provide an interface to the sensor;
a data digitizer coupled to the sensor reader to convert sensor data for transmission over a digital medium; and
a data encoder coupled to the digitizer to encode the sensor data.

106. The system of claim 105, wherein the sensor includes a pressure-based sensor.

107. The system of claim 106, wherein the sensor includes a piezoelectric crystal.

108. The system of claim 106, wherein the sensor includes a capacitive membrane sensor.

109. The system of claim 105, wherein the sensor includes an oxygen sensor.

110. The system of claim 105, wherein the sensor includes an impedance sensor.

111. The system of claim 105, wherein the sensing circuitry is fabricated using Micro-Electro-Mechanical Systems (MEMS) technology.

112. The system of claim 105, wherein the sensing circuitry is further adapted to sense electrical parameters in the biosystem.

113. The system of claim 105, wherein the sensing circuitry is further adapted to sense chemical parameters in the biosystem.

114. The system of claim 105 wherein the stent-like structure is adapted to be chronically placed intravascularly in the biosystem.

115. A system, comprising:
a planet; and
at least one satellite device adapted to communicate with the planet, wherein the satellite device includes;
a stent-like structure adapted to be chronically placed within a vessel of a biosystem;
sensing circuitry attached to the structure and adapted to be placed in the vessel with the structure, wherein the sensing circuitry is adapted to sense mechanical parameters in the biosystem; and
therapy-providing circuitry attached to the structure and adapted to be placed in the vessel with the structure, wherein the therapy-providing circuitry is adapted to provide therapy to the biosystem and further includes;
an output capacitor charging circuit;
a set parameters circuit for adjusting stimulation parameters;
an electrical application circuit operably connected to the output capacitor charging circuit and the set stimulation parameters circuit to provide an electrical signal; and
at least one electrode operably connected to the electrical application circuit and adapted to provide electrical therapy.

116. The system of claim 115, wherein the set stimulation parameters circuits adapted to adjust pulse width, amplitude stimulation modes, and stimulation site.

117. The system of claim 115, wherein the electrical application circuit includes an inject current circuit.

118. The system of claim 115, wherein the electrical application circuit includes a set voltage circuit.

119. The system of claim 115 wherein the therapy-providing circuitry is adapted to provide pacing therapy to a heart.

120. The system of claim 115, wherein the therapy-providing circuitry is adapted to provide defibrillation therapy to a heart.

121. The system of claim 115 wherein the stent-like structure is adapted to be chronically placed intravascularly in the biosystem.

122. A system, comprising:
a planet; and
at least one satellite device adapted to communicate with the planet, wherein the satellite device includes;
a structure adapted to be chronically placed within a vessel of a biosystem;
sensing circuitry attached to the structure and adapted to be placed in the vessel with the structure, wherein the sensing circuitry is adapted to sense mechanical parameters in the biosystem; and
therapy-providing circuitry attached to the structure and adapted to be placed in the vessel with the structure, wherein the therapy-providing circuitry is adapted to provide therapy to the biosystem and further includes;
drug-eluting circuitry, including;
an active substrate;
an electro-erodible covering enclosing the active substance; and
electrodes adapted to controllably erode the electrode covering to controllably release the active substrate.

123. The system of claim 122, wherein the electrodes are addressable to control the drug-eluting process.

124. The system of claim 122, wherein the electro-erodible covering is tapered to control the drug-eluting process.

125. The system of claim 122, wherein the therapy-providing circuitry is adapted to provide drug-eluting therapy in response to a heart-attack.

126. The system of claim 122, wherein the therapy-providing circuitry is adapted to provide drug-eluting therapy in response to a stroke.

127. The system of claim 122, wherein the therapy-providing circuitry is adapted to provide appropriate therapy in response to a sensed blood sugar level that is out of a desired range.

128. The system of claim 122, wherein the structure includes a stent-like structure adapted to be chronically placed in the biosystem.

129. The system of claim 128, wherein the stent-like structure is adapted to be chronically placed intravascularly in the biosystem.

130. A method, comprising:
inserting a stent-like device intravascularly into a biosystem;
sensing a mechanical parameter using the device; and
providing electrical therapy using the device.

131. The method of claim 130, wherein inserting a device intravascularly includes inserting a plurality of devices intravascularly to function together as a system.

132. The method of claim 130, wherein inserting a device intravascularly includes arterially inserting a device.

133. The method of claim 130, wherein sensing a mechanical parameter includes sensing blood pressure.

134. The method of claim 130, wherein sensing a mechanical parameter includes sensing blood flow.

135. The method of claim 130, wherein sensing a mechanical parameter includes sensing vessel size.

136. The method of claim 130, further comprising sensing oxygen.

137. The method of claim 130, further comprising sensing ions.

138. The method of claim 130, further comprising sensing coagulation.

139. The method of claim 130, further comprising sensing fibrosis.

140. The method of claim 130, further comprising sensing intrinsic electrical signals generated by excitable tissue.

141. The method of claim 130, wherein providing therapy includes stimulating electrically excitable tissue.

142. The method of claim 141, wherein stimulating electrically excitable tissue includes providing cardiac stimulus signals.

143. The method of claim 130, wherein providing therapy includes eluting drugs to improve biocompatibility.

144. The method of claim 130, wherein providing therapy includes eluting drugs in response to a detected stroke condition.

145. The method of claim 130, wherein providing therapy includes eluting drugs in response to a detected heart attack condition.

146. The method of claim 130, wherein providing therapy includes eluting an active substance in response to a sensed blood sugar level.

147. A device, comprising:
a stent-like structure adapted to be chronically placed within a vessel of a biosystem;
sensing circuitry attached to the structure and adapted to be placed in the vessel with the structure, wherein the sensing circuitry includes a chemical sensor; and
therapy-providing circuitry attached to the structure and adapted to be placed in the vessel with the structure, wherein the therapy-providing circuitry is adapted to provide electrical therapy to the biosystem.

148. A device, comprising:
a stent-like structure adapted to be chronically placed within a vessel of a biosystem;
sensing circuitry attached to the structure and adapted to be placed in the vessel with the structure, wherein the sensing circuitry includes a biosensor; and
therapy-providing circuitry attached to the structure and adapted to be placed in the vessel with the structure, wherein the therapy-providing circuitry is adapted to provide electrical therapy to the biosystem.

149. An implantable stimulation system for stimulating a patient's heart, comprising:
an implantable stimulation device, adapted to be implanted within a blood vessel of the heart, including:
a pulse generator to generate electrical stimulation for the heart; and
a sensing circuit coupled to the pulse generator; and
a stent-like support structure to retain the implantable stimulation device within the blood vessel.

150. An implantable stimulation system for stimulating a patient's heart comprising:
an implantable stimulation device, adapted to be implanted within a blood vessel of the heart, including:
a pulse generator to generate electrical stimulation for the heart; and
a sensing circuit coupled to the pulse generator;
a support structure to retain the implantable stimulation device within the blood vessel; and
an electrode to deliver electrical stimulation to the heart upon detection by the sensing circuit of an arrhythmia.

151. An implantable stimulation system for stimulating a patient's heart comprising:
an implantable stimulation device adapted to be implanted within a blood vessel of the head including:
a pulse generator to generate electrical stimulation for the heart; and
a sensing circuit coupled to the pulse generator:
a support structure to retain the implantable stimulation device within the blood vessel; and
an electrode formed on the support structure to deliver electrical stimulation to the heart upon detection by the sensing circuit of an arrhythmia.

152. The implantable stimulation system of claim 150, further comprising:
a housing for the implantable stimulation device;
wherein the housing or part of the housing forms the electrode.

153. The implantable stimulation system of claim 149, the implantable stimulation device further including a battery.

154. The implantable stimulation system of claim 149, the implantable stimulation device further including a capacitor.

155. An implantable stimulation device for stimulating a patient's heart, comprising:
a pulse generator, adapted to be implanted within a blood vessel, to generate electrical stimulation for the heart;
a sensing circuit coupled to the pulse generator; and
an electrode to deliver electrical stimulation to the heart upon detection by the sensing circuit of an arrhythmia.

156. The implantable stimulation device of claim 155, wherein the sensing circuit is implanted within the blood vessel.

157. The implantable stimulation device of claim 155, further comprising a lead to connect the electrode to the pulse generator.

158. The implantable stimulation device of claim 155, further comprising a housing to encapsulate the pulse generator and sensing circuit, wherein the housing or part of the housing forms the electrode.

159. The implantable stimulation device of claim 155, further comprising a battery.

160. The implantable stimulation device of claim 155, further comprising a capacitor.

161. A method of implanting a stimulation device for electrically stimulating a patient's heart, the method comprising:
placing the stimulation device into a coronary vessel; and
expanding a support structure to hold the stimulation device in place within the coronary vessel.

162. The method of claim 161, further comprising the step of using a catheter to move the support structure to a desired location within the coronary vessel.

163. The method of claim 161, wherein the stimulation device is a pulse generator.

164. The method of claim 161, wherein at least one lead is attached to the pulse generator.

165. The method of claim 163, wherein the at least one lead includes at least one electrode.

166. The method of claim 163, wherein the pulse generator includes at least one electrode.

167. The method of claim 162, further comprising the step of releasing the support structure from the catheter, and wherein the expanding step includes causing the support structure to self-expand.

168. The method of claim 162, further comprising the step of releasing the support structure from the catheter, and wherein the expanding step includes positioning an expansion device within the support structure and expanding the expansion device.

169. The method of claim 168, wherein the expansion device is a balloon.

170. The method of claim 161, further comprising the step of positioning at least one electrode in a coronary vessel or a chamber of the patient's heart, the at least one electrode being coupled to the stimulation device.

171. The method of claim 170, wherein the at least one electrode is attached to a lead.

172. An implantable stimulation system for stimulating a patient's heart, comprising:
an implantable stimulation device, adapted to be implanted within a blood vessel, comprising a pulse generator to generate electrical stimulation for the heart said implantable stimulation device including a stent-like structure; and
at least one electrode to deliver electrical stimulation to the heart.

* * * * *

UNITED STATES PATENT AND TRADEMARK OFFICE
CERTIFICATE OF CORRECTION

| | | |
|---|---|---|
| PATENT NO. | : 7,236,821 B2 | Page 1 of 2 |
| APPLICATION NO. | : 10/079056 | |
| DATED | : June 26, 2007 | |
| INVENTOR(S) | : Cates et al. | |

It is certified that error appears in the above-identified patent and that said Letters Patent is hereby corrected as shown below:

In claim 32, column 30, line 14, "(RE)" should read --(RF)--.

*In claim 38, column 30, line 30, "extract or" should read --extractor--.

In claim 40, column 30, line 36, "Includes" should read --includes--.

In claim 41, column 30, line 39, "includes;" should read --includes:--.

In claim 41, column 30, line 43, "date" should read --data--.

In claim 41, column 30, line 48, "includes;" should read --includes:--.

In claim 45, column 31, line 10, "including;" should read --including:--.

In claim 45, column 31, line 19, "includes;" should read --includes:--.

In claim 45, column 31, line 24, "active;" should read --active substrate;--.

In claim 50, column 31, line 49, "ant-like" should read --stent-like--.

In claim 50, column 31, line 57, "ached" should read --attached--.

In claim 50, column 31, line 57, "ant-like" should read --stent-like--.

In claim 51, column 31, line 62, "ant-like" should read --stent-like--.

In claim 51, column 31, line 63, "Intravascularly" should read --intravascularly--.

In claim 87, column 33, line 51, "(RE)" should read --(RF)--.

In claim 92, column 34, line 9, "includes;" should read --includes:--.

In claim 99, column 34, line 36, "RE" should read --RF--.

In claim 102, column 34, line 42, "(RE)" should read --(RF)--.

In claim 115, column 35, line 16, "includes;" should read --includes:--.

In claim 115, column 35, line 26, "includes;" should read --includes:--.

In claim 121, column 35, line 49, "115" should read --115,--.

UNITED STATES PATENT AND TRADEMARK OFFICE
CERTIFICATE OF CORRECTION

PATENT NO. : 7,236,821 B2
APPLICATION NO. : 10/079056
DATED : June 26, 2007
INVENTOR(S) : Cates et al.

It is certified that error appears in the above-identified patent and that said Letters Patent is hereby corrected as shown below:

In claim 122, column 35, line 55, "includes;" should read --includes:--.

In claim 122, column 35, line 66, "including;" should read --including:--.

In claim 151, column 37, line 44, "head" should read --heart,--,

In claim 151, column 37, line 47, "generator:" should read --generator;--.

In claim 172, column 38, line 59, "heart" should read --heart,--.

Signed and Sealed this

Seventh Day of August, 2007

JON W. DUDAS
*Director of the United States Patent and Trademark Office*

(12) INTER PARTES REEXAMINATION CERTIFICATE (679th)

United States Patent
Cates et al.

(10) Number: US 7,236,821 C1
(45) Certificate Issued: Aug. 27, 2013

(54) CHRONICALLY-IMPLANTED DEVICE FOR SENSING AND THERAPY

(75) Inventors: Adam W. Cates, Minneapolis, MN (US); Paul V. Goode, San Diego, CA (US); Scott T. Mazar, Inver Grove Heights, MN (US)

(73) Assignee: Cardiac Pacemakers, Inc., St. Paul, MN (US)

Reexamination Request:
No. 95/000,330, Dec. 17, 2007

Reexamination Certificate for:
Patent No.: 7,236,821
Issued: Jun. 26, 2007
Appl. No.: 10/079,056
Filed: Feb. 19, 2002

Certificate of Correction issued Aug. 7, 2007

(51) Int. Cl.
*A61N 1/00* (2006.01)

(52) U.S. Cl.
USPC .......................................................... 607/2

(58) Field of Classification Search
None
See application file for complete search history.

(56) References Cited

To view the complete listing of prior art documents cited during the proceeding for Reexamination Control Number 95/000,330, please refer to the USPTO's public Patent Application Information Retrieval (PAIR) system under the Display References tab.

*Primary Examiner* — David O. Reip

(57) ABSTRACT

Systems, devices and methods are provided for providing sensing and therapy functions using a chronically-implanted device. According to one embodiment, the device includes a structure adapted to be chronically placed within a biosystem, and further includes sensing circuitry and therapy-providing circuitry attached to the structure. The sensing circuitry is adapted to sense mechanical parameters in the biosystem. The therapy-providing circuitry is adapted to provide therapy to the biosystem. According to various embodiments of the device, the sensing circuitry is further adapted to sense electrical and/or chemical parameters in the biosystem, and/or is adapted to provide electrical therapy and/or to provide drug-eluting therapy. One embodiment of the device includes a stent-like structure adapted to be chronically placed intravascularly in the biosystem.

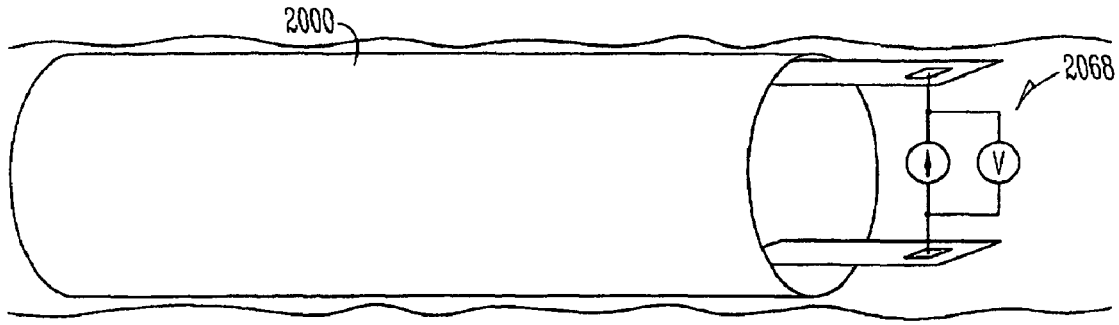

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claims 150-152, 156 and 158 is confirmed.

Claims 149, 153-155, 157 and 159-172 are cancelled.

Claims 1-148 were not reexamined.

\* \* \* \* \*